US009044459B2

(12) United States Patent
Perrin et al.

(10) Patent No.: US 9,044,459 B2
(45) Date of Patent: Jun. 2, 2015

(54) METHOD FOR THE TREATMENT OF NEURODEGENERATIVE DISEASES

(71) Applicant: ALS Therapy Development Institute, Cambridge, MA (US)

(72) Inventors: Steven Perrin, Newbury, MA (US); John Monteith Lincecum, Jamaica Plain, MA (US); Alan Gill, Reading, MA (US); Fernando Vieira, Boston, MA (US)

(73) Assignee: ALS THERAPY DEVELOPMENT INSTITUTE, Cambridge, MA (US)

( * ) Notice: Subject to any disclaimer, the term of this patent is extended or adjusted under 35 U.S.C. 154(b) by 116 days.

(21) Appl. No.: 13/858,667

(22) Filed: Apr. 8, 2013

(65) Prior Publication Data
US 2013/0295092 A1 Nov. 7, 2013

Related U.S. Application Data

(63) Continuation of application No. 13/132,670, filed as application No. PCT/US2009/066715 on Dec. 4, 2009, now Pat. No. 8,435,514.

(60) Provisional application No. 61/120,121, filed on Dec. 5, 2008.

(51) Int. Cl.
| *A61K 39/395* | (2006.01) |
| *C07K 16/28* | (2006.01) |
| *A61K 45/00* | (2006.01) |
| *A61K 45/06* | (2006.01) |
| *A61K 38/17* | (2006.01) |
| *A61K 39/00* | (2006.01) |

(52) U.S. Cl.
CPC ............ *A61K 39/3955* (2013.01); *A61K 45/00* (2013.01); *A61K 45/06* (2013.01); *A61K 38/1774* (2013.01); *A61K 39/395* (2013.01); *C07K 16/2875* (2013.01); *A61K 2039/505* (2013.01); *C07K 2317/21* (2013.01)

(58) Field of Classification Search
None
See application file for complete search history.

(56) References Cited

U.S. PATENT DOCUMENTS

| 6,001,358 A | 12/1999 | Black et al. |
| 7,169,389 B2 | 1/2007 | DiPadova et al. |
| 7,863,419 B2 | 1/2011 | Taylor et al. |
| 8,435,514 B2 * | 5/2013 | Perrin et al. ............ 424/130.1 |
| 2007/0190053 A1 | 8/2007 | Kalled et al. |
| 2011/0172400 A1 | 7/2011 | Grant et al. |

FOREIGN PATENT DOCUMENTS

| WO | 01/83755 A2 | 11/2001 |
| WO | 2004/037204 A2 | 5/2004 |
| WO | 2006/138316 A2 | 12/2006 |

OTHER PUBLICATIONS

Cicchetti et al., Trends in Pharmacological Sciences (2009) 30: 475-483.*
Vainzof et al., J. Mol. Neurosci. (2008) 34: 241-248.*
Abcam, 2012, 2 pgsq.
Amyotrophic Lateral Sclerosis (ALS) Fact Sheet, NIH Internet Publication relating to ALS accessed Nov. 19, 2012.
Bosco, D. A., et al., "Wild-type and mutant SOD1 share an aberrant conformation and a common pathogenic pathway in ALS", Nat Neurosci, 2010, vol. 13, No. 11, pp. 1396-1403.
Building a Better Mouse, MDA/ALS Newsmagazine, Sep. 1, 2010.
Dumont, F.J., "IDEC-131. IDEC/Eisai" Curr Opin Invenstig Drugs, 2002, vol. 3, No. 5, pp. 725-734 Abstract.
Gilliland, L. K., "Rapid and Reliabie Cloining of Antibody Variable Regions and Generation of Recombinant Single Chain Antibody Fragments", Tissue Antigens, 1996, vol. 47, pp. 1-20.
Gruzman, A., et al., "Common Molecular Signature in SOD1 for both Sporadic and Familial Amyotrophic Lateral Sclerosis", PNAS, 2007, vol. 104, No. 30, pp. 12524-12529.
Imgenex, accessed Sep. 21, 2012, 2 pgs.
Ke, Zun-Ji, et al., "CD4O-CD40L Internactions Promote Neuronal Death in a Model of Neurodegeneration Due to Miled Impairment of Oxidatice Metabolism", Neurochemistry International, 2005, vol. 47, pp. 204-215.
Kiaei, Mahmoud, et al., "Celastrol Blocks Neuronal Cell Death and Extends Life in Transgenic Mouse Model of Amyotrophic Lateral Sclerosis", Neurodegenerative Dis, 2005, vol. 2, No. 5, pp. 246-254.
Kirk, A. D., et al., "CTLA4-Ig and anti-CD40 Ligand Prevent Renal Allograft Rejection in Primates", Proc Natl Acad Sci USA, 1997, vol. 94, pp. 8789-8794.
Knosalla, C. R., et al., "Intial Experience with the Humna Anti-human CD154 Monoclonal Antibody, ABI793, in Pig-to-baboon Xenotransplantation", Xenotransplantation, 2004, Vol, 11, pp. 353-360.
Law, C. et al., "Preclinical Antilymphoma Activity of a Human Anti-CD40 Monoclonal Antibody, SGN-40", Cancer Res, 2005, vol. 65, No. 18, pp. 8331-88338.
Lederman, S. et al., Identification of a Novel Surface Protein on Activated CD4+ T Cells that Induces Contact-dependent B Cell Differentiation (Help), J Exp Med, 1992, vol. 175, pp. 1091-1101.
Leitner, M., et al., Working with ALS Mice:, The Jackson Laboratory, Oct. 14, 2009.
Lincecum, J. M., et al., "From Transcriptome Analysis to Therapeutic anti-CD4OL Treatement in the SOD1 Model of Amyotrophic Lateral Sclerosis". Nature Genetics, 2010, pp. 1-10.
Ludolph, A. C., et al., "Guidelines for Preclinical Animal Research in ALS/MND: A Consensus Meeting", Amyotrophic Lateral Sclerosis, 2010, vol. 11, pp. 38-45.
PCT/US2009/066715 International Search Report dated Mar. 22, 2010.

(Continued)

*Primary Examiner* — Ilia Ouspenski
(74) *Attorney, Agent, or Firm* — Honigman Miller Schwartz and Cohn LLP; Cynthia M. Bott; Jonathan P. O'Brien

(57) ABSTRACT

Disclosed are methods for treating neurodegenerative diseases such as Amyotrophic Lateral Sclerosis, Alzheimer's Disease Parkinson's Disease, Myasthenia Gravis, Multifocal Motor Neuropathy, Primary Lateral Sclerosis, Spinal Muscular Atrophy, Kennedy's Disease, and Spinocerebellar Ataxia.

4 Claims, 26 Drawing Sheets

(56) References Cited

OTHER PUBLICATIONS

Santa Cruz Biotechnology Inc., accessed Sep. 21, 2012, 1 pg.

Tai, Y., et al., "Mechanisms by Which SGN-40, a Humanized Anti-CD40 Antibody, Induces Cytotoxicity in Human Multiple Myeloma Cells: Clinical Implications", Cancer Rersearch, 2004, vol. 64, pp. 2846-2852.

Van Blitterswijk, M. et al., "Anti-superoxide Dismutase Antibodies are Associated with Survival in Patients with Sporadic Amyotrophic Lateral Sclerosis", Amyotroph Lateral Scler, 2011, vol. 12, No. 6, pp. 430-438.

Viglietta, V. et al., "CTLA4Ig Treatment in Patients With Multiple Sclerosis", Neurology, 2008, vol. 71, No. 12, pp. 917-924.

Sakoda, Saburou, "Study on a breakthrough technique to diagnosis or treat amyotrophic lateral sclerosis—Analysis of CD40 in amyotrophic lateral sclerosis"—Report of 2006 Houkatsu Kenkyuu, 2007, pp. 51-53 (in Japanese).

Sakoda, Saburou, "Study on a breakthrough technique to diagnosis or treat amyotrophic lateral sclerosis—Analysis of CD40 in amyotrophic lateral sclerosis"—Report of 2006 Houkatsu Kenkyuu, 2007, pp. 51-53 (English translation).

\* cited by examiner

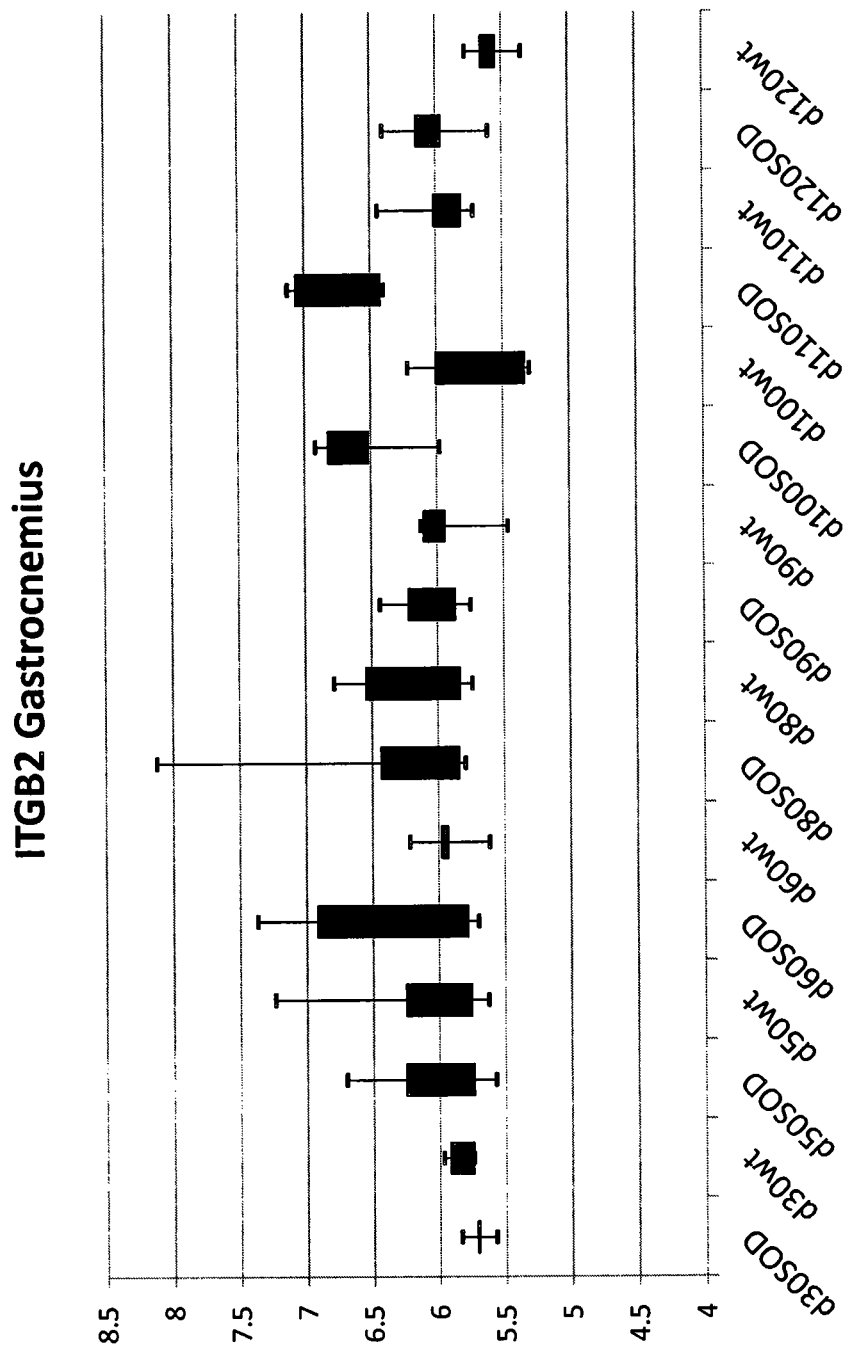

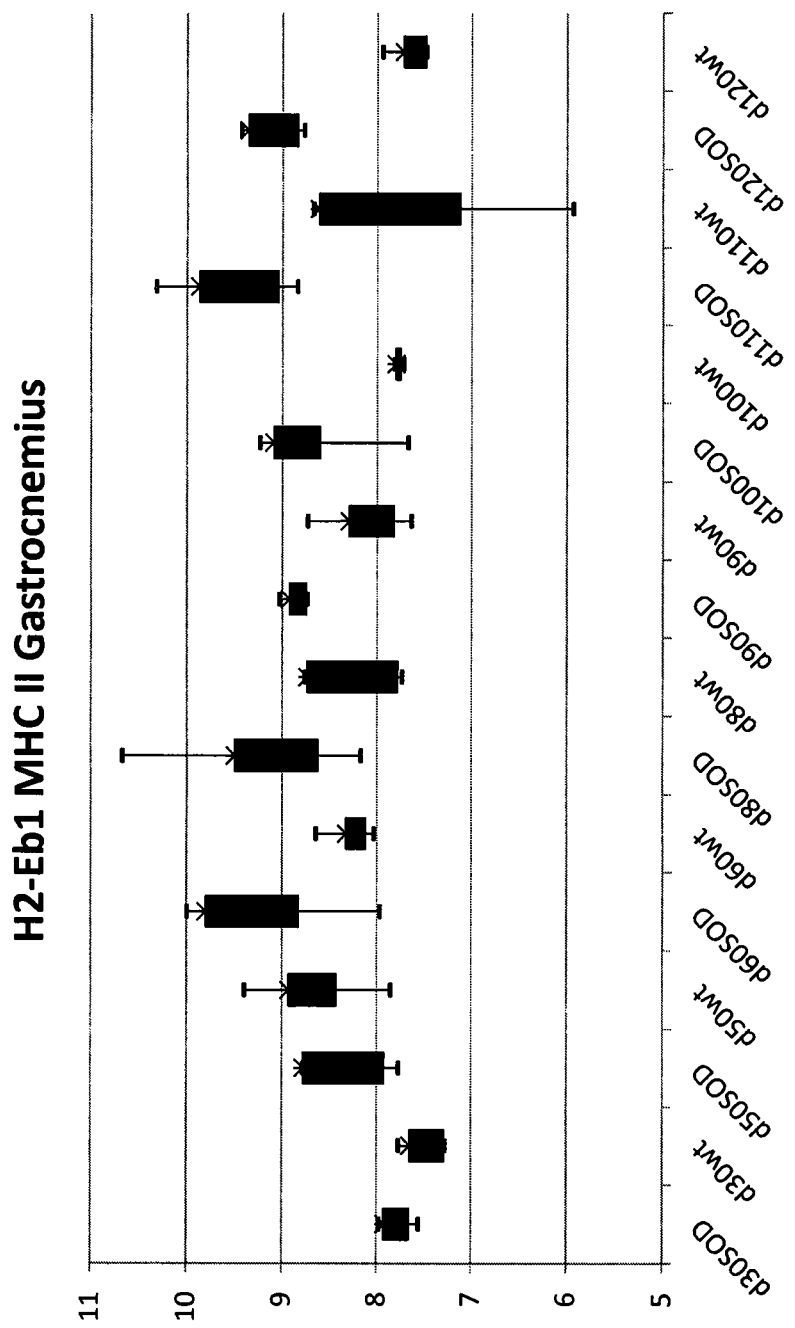

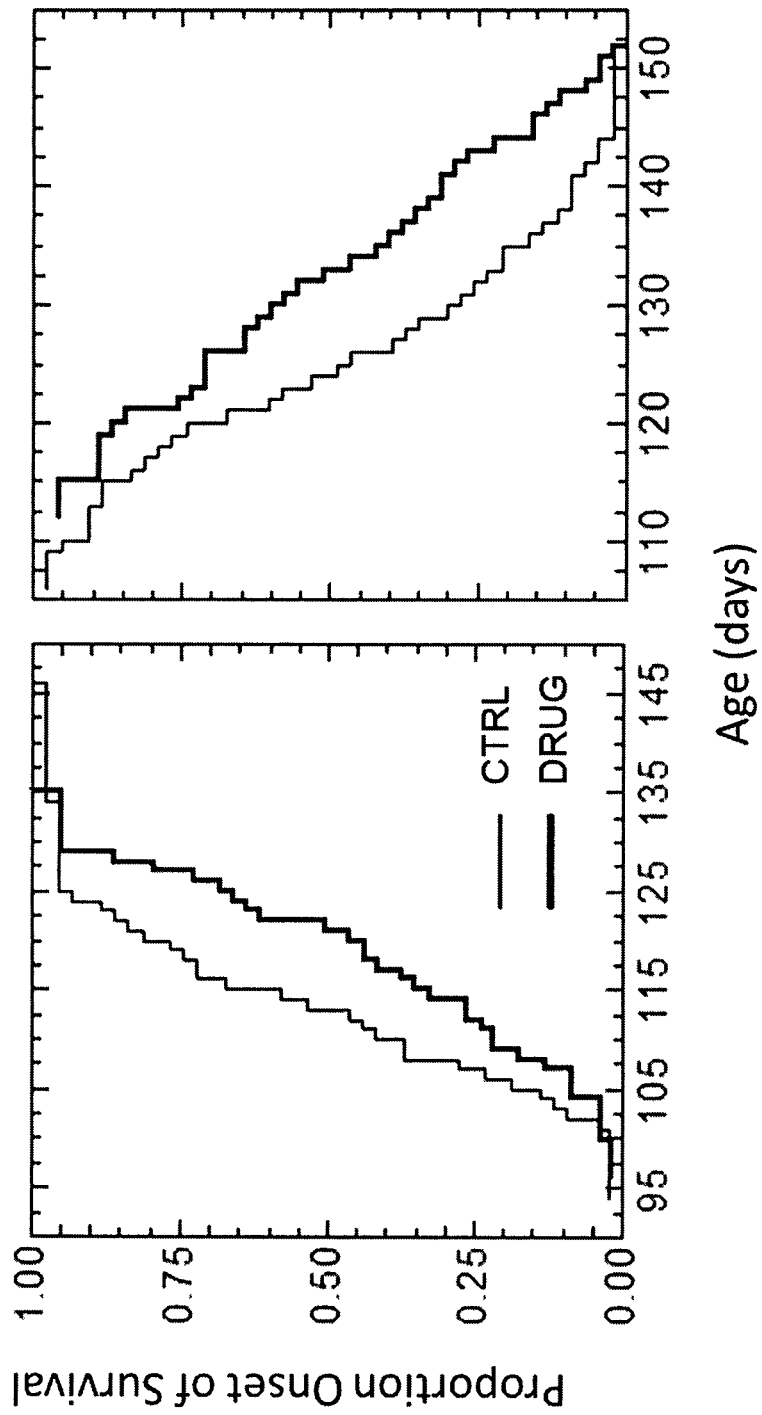

METHOD FOR THE TREATMENT OF NEURODEGENERATIVE DISEASES

CROSS REFERENCE TO RELATED APPLICATIONS

This application is a continuation of U.S. application Ser. No. 13/132,670, which is a National Phase application of PCT/US2009/066715 filed Dec. 4, 2009, and claims priority to U.S. Provisional Application Ser. No. 61/120,121 filed Dec. 5, 2008. The entire contents of each of which are hereby incorporated herein by reference.

TECHNICAL FIELD OF THE INVENTION

The present invention relates to methods for treating neurodegenerative diseases such as Amyotrophic Lateral Sclerosis, Alzheimer's Disease Parkinson's Disease, Myasthenia Gravis, Multifocal Motor Neuropathy, Primary Lateral Sclerosis, Spinal Muscular Atrophy, Kennedy's Disease, and Spinocerebellar Ataxia.

BACKGROUND

Amyotrophic lateral sclerosis (ALS), sometimes called Lou Gehrig's Disease, is a progressive, fatal, neurological disorder characterized by muscle fiber atrophy resulting from the degeneration of motor neurons in the spinal column and brain. ALS affects approximately 30,000 US citizens with only about 10% of the cases being classified as the familial form of ALS. In a subset of familial patients with mutations in the metabolic enzyme superoxide dismutase 1 (SOD1), the pathological progression may be attributed to an unknown gain of function associated with a mutant form of the enzyme (SOD1 dependant) (Rosen, 1993). However in the majority of ALS cases the SOD1 gene contains no mutations, the activity of the SOD1 enzyme is normal, and the mechanism of disease pathology is unknown (SOD1 independent). Therefore the remaining 90% of ALS cases are classified as sporadic cases with no well characterized genetic component or causal agent.

Because the cause of the sporadically occurring form of the disease is unknown, researchers have turned to transgenic strategies to create laboratory models of the disease. Identification role of the SOD1 gene has led to the generation of transgenic rodent models of ALS. A transgenic mouse strain carrying 23 copies of the human SOD1$^{G93A}$ transgene (the "G93A mouse") is the most widely used murine model of ALS and is accepted as a standard model for ALS therapeutic studies (the "G93A mouse") (see Tu P H et. al. (1996) *Proc Natl Acad Sci USA* 93:3155-3160 and Gurney M E (1997) *J Neuro Sci* 152 Suppl 1: S67-S73)

Although ALS is characterized by loss of motor neurons in the spinal cord resulting in muscle atrophy, the disease also manifests itself with changes in axon transport, protein aggregation, excitotoxicity, astrocytosis, mitochondrial dysfunction, microglial activation, and synaptic remodeling. Microglial activation, astrocytosis and the presence of infiltrating inflammatory cells from the periphery has been well described. There is accumulation of IgG immunoreactive deposits in the spinal cord of ALS patients, infiltration of lymphocytes, dendritic cells, monocytes, and macrophages into the spinal cord in ALS. Although the role of infiltrating immune cells is poorly understood, recent work would suggest that infiltrating T cell populations are neuroprotective and not cytotoxic. Although ALS has an immune component mediated by activation of microglia and astrocytes it is not considered to be an autoimmune disorder. Unlike diseases such as rheumatoid arthritis or systemic lupus erythematosus in which involvement of specific immune modulatory pathways (e.g., the costimulatory pathway) has been described, involvement of such pathways has not been described for ALS.

Currently physicians have limited choices for treating ALS. At this time, riluzole is the only drug that has been approved by the FDA for treatment of ALS. In clinical trials, riluzole has shown only a slight benefit in modestly increasing survival time. Thus there is an urgent need for effective therapies for ALS.

BRIEF SUMMARY

According to the present disclosure are methods of treating a patient with a neurodegenerative or neuromuscular disorder by administering a therapeutically effective amount of a compound that blocks the interaction of CD40 and CD40L. Also according to the present disclosure are methods of treating a patient with a neurodegenerative or neuromuscular disorder by administering anti-CD40L antibodies or, anti-CD40 antibodies or, small molecules.

Disorders which may be treated according to the present disclosure include, but are not limited to, Alzheimer's Disease, Parkinson's Disease, Amyotrophic Lateral Sclerosis, Myasthenia Gravis, Multifocal Motor Neuropathy, Primary Lateral Sclerosis, Spinal Muscular Atrophy, Kennedy's Disease, or Spinocerebellar Ataxia.

In some methods of the present disclosure, the patient with a neurodegenerative or neuromuscular disorder is treated with a compound that blocks the interaction of CD40 and CD40L in combination with a compound that blocks the interaction between CD28 and CD86 or between CD28 and CD80.

BRIEF DESCRIPTION OF THE DRAWINGS

FIG. 9C shows the time to disease onset based on the time to progress to a neurological score of 2 in the control group and the MR1 treated group.

FIG. 9D shows the mean daily body weight measurements from peak body weight to death for the control and the MR1 treated group.

DETAILED DESCRIPTION

I. Introduction

Figure 1A:
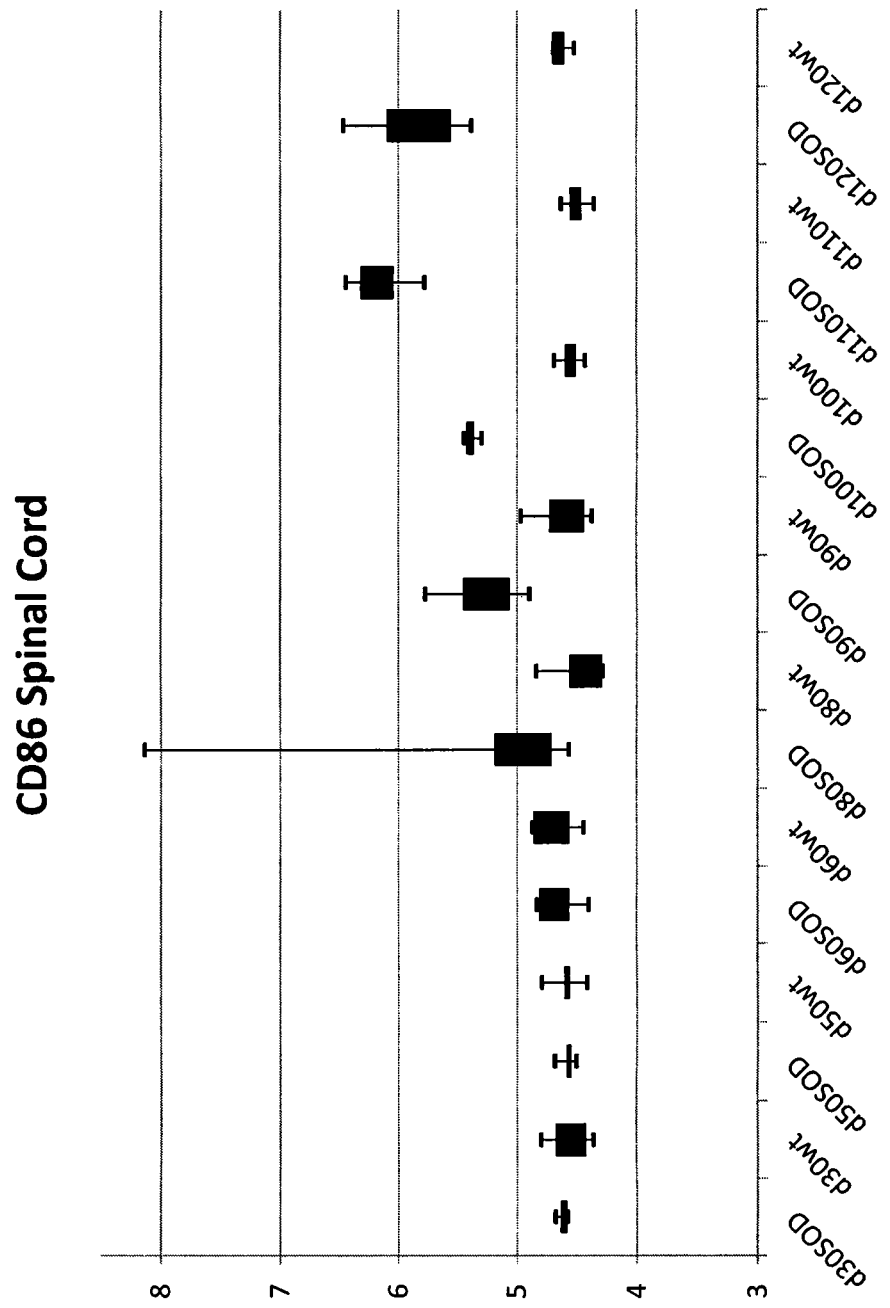
FIGS. 1A-P depict the temporal changes in RNA expression patterns of genes associated with induction of the costimulatory pathway in the spinal cord and gastrocnemius muscle of the G93A mouse model.

The present disclosure describes methods of treating a patient with a neurodegenerative or neuromuscular disorder by administering a therapeutically effective amount of a compound that blocks the interaction of CD40 and CD40L. The disclosure also describes methods of treating patients by co-administering a compound that blocks the interaction of CD40 and CD40L with a compound that blocks the interactions blocks the interaction between CD28 and CD86 or between CD28 and CD80.

II. Abbreviations and Definitions

The following abbreviations are used herein: amyotrophic lateral sclerosis (ALS); super oxide dismutases-1 (SOD1); T cell receptor (TCR); major histocompatibility complex (MHC) antigen presenting cell (APC); Phosphate buffered saline (PBS), complementarity determining regions (CDR). "IP" means intraperitoneally and "IV" means intravenously.

MR1 is a hamster monoclonal antibody that binds to mouse CD40 ligand. "Wild type" as used herein means a non-transgenic mouse. As used herein "small molecule" means a compound having a molecular weight of less than 2000 Daltons. "Treatment" or "treating" as used herein includes prophylactic and therapeutic treatment. The phrase "therapeutically effective amount" means an amount of a compound, or a pharmaceutically acceptable salt thereof, sufficient to inhibit, or allow an improvement in the disorder or condition being treated with administered alone or in conjunction with another pharmaceutical agent or treatment in a particular subject or subject population. "ALS-TDI" is an abbreviation for ALS Therapy Development Institute. "hSOD1G93A preclinical mouse model", "hSOD1G93A mouse model", "G93A preclinical mouse model" and "G93A mouse model" have the same meaning as used herein. "hSOD1G93A mouse" and "G93A mouse" have the same meaning as used herein.

III. In Vivo Evaluation of Compounds

Compounds used in the methods of the present disclosure may be evaluated for their efficacy using the G93A mouse model, [see Tu P H et al. Proc Natl Acad Sci USA 1996; 93:3155-60 and Gurney M E. et al. J Neurol Sci 1997; 152 (Suppl 1):S67-73]. This model was constructed by inserting 23 copies of the human SOD1 gene, which contains a glycine to alanine mutation at position 93, into the mouse genome. These mice accurately recapitulate most major points of pathology of the human sporadic and familial forms of the disease making this model the best currently available option for testing disease altering interventions.

There is no discernable phenotypic expression of the abnormality in the G93A mouse at birth. Visible disease signs do not express until about 90 days of age, whereupon it experiences a progressive loss of hindlimb function resulting in complete paralysis and death around 134 days of age. While muscle wasting is caused by the death or dysfunction of motor neurons, the death of these cells is associated with and partially caused by interactions with surrounding cells including microglia and astrocytes. A pronounced astrocytosis first appears around 80 days of age while a neuroinflammation, mediated mainly by microglia, appears around 100 days of age and expands until death.

While the human disease may begin in any motor region, the mouse disease reliably affects the cervical and lumbar regions first. In the G93A mouse, motor neuron numbers have declined significantly by the time of visible symptom onset, at approximately day 85, and reach upwards of 50% loss at death. Abnormalities in the cytoskeleton, neurofilaments, axonal transport, golgi, endoplasmic reticulum, mitochondria, apoptotic machinery, proteasome, and cytosolic protein handling are observed in neurons during the course of the disease.

While the human disease may begin in any motor region, the mouse disease reliably affects the lumbar and sacral regions first. In the G93A mouse, motor neuron numbers have declined significantly by the time of visible symptom onset, at approximately day 85, and reach upwards of 50% loss at death. Abnormalities in the cytoskeleton, neurofilaments, axonal transport, golgi, endoplasmic reticulum, mitochondria, apoptotic machinery, proteasome, and cytosolic protein handling are observed in neurons during the course of the disease.

To date, there have been at least 50 publications describing therapeutic agents that extend the lifespan of this mouse. However, no therapeutic agent other than riluzole has show corresponding clinical efficacy. The ALS Therapy Development Institute has described optimized therapeutic drug screening in the G93A mouse model which controls for noise variables [Scott S. et al. *Amyotrophic Lateral Sclerosis* 2008; 9: 4-15 which is hereby incorporated by reference]. Scott et al. describe a minimum study design for the G93A mouse model which addresses and manages the noise caused by the inherent confounding biological variables. In validating this study design, nine compounds that had previously been reported to be efficacious on in the preclinical model and subsequently failed in human clinical trials, were evaluated, most at varying doses, Several of these molecules are anti-inflammatory molecules that inhibit tumor necrosis factor signaling (TNF) and microglial activation including Celebrex®, minocycline, thalidomide, and creatine. Celebrex® was reported to improve lifespan in the G93A model by 19% (24 days) yet a high powered study failed to detect any change in survival (1.8 days, 0.52%), (Scott et al.). Similar results were obtained by for minocycline (previously reported; 15.8% improvement; high powered study, −0.60%), creatine (previously reported 17.8%; high powered study 0.67%), and thalidomide (previously reported 16% improvement in survival; high powered study −1.9%).

IV. Identification of Candidate Compounds

As described in detail in Example 1, genome wide expression profiling analysis was performed for wildtype mice and G93A mice at various time points during disease progression. Genes identified as differentially expressed between the two groups were analyzed and the resulting data were used to focus the selection of drugs to be screened. Among the genes that were differentially expressed include genes involved in the immune response and cell adhesion including CD86, CD44, ICAM, ITGAM, ITGA ITGAX, ITGB2, H2-K1 (MHC II), H2-AB1 (MHC II), H2-D1 (MHCII), and H2-Eb1 (MHC II). These data show that inflammatory signatures increase during disease progression and are consistent with the involvement of co-stimulatory pathway. The co-stimulatory pathway involves interactions between cell types via CD28/CD80 or CD28/CD86 or CD40/CD40L interactions some of which were identified in the gene expression analysis.

The co-stimulatory pathway involves, along with other interactions, the binding of CD40 on B cells to CD40L (also known as CD154, gp39, T-BAM, 5c8 antigen, CD40CR and TRAP) on T cells. Human CD40 is expressed on mature B cells, as well as macrophages, dendritic cells, fibroblasts and activated endothelial cells. It is thought that blockade of the CD40:CD40L binding promotes the development of Type I T-helper cell responses.

Using compounds that block these interactions and inhibit the co-stimulatory signals, a significant body of work has demonstrated the immunomodulatory effects of blocking one or more of CD40L, CD80 or CD86 in preclinical models of transplantation and autoimmunity. Blocking CD40L function with blocking antibodies or adenoviral expression of CD40L-Ig improves allograft transplant by 30 to 90 days. Similar studies blocking CD80/CD86 on APCs with CTLA4-Ig or adenoviral expression of CTLA4-Ig transiently improves allograft transplant survival, Transplant rejection in these models is transient and graft rejection ensues over time. Longer term repression of transplant rejection can be accomplished by blocking both the co-stimulatory pathway with CTLA4-Ig and blocking CD40L activation of APCs with anti-CD40L antibodies.

Blocking antibodies to CD40L or genetic deletion of CD40L in mice has demonstrated that CD40L ameliorates disease progression, survival, and surrogate markers of disease in preclinical models of experimental allergic encephalomyelitis (EAE) a model of multiple sclerosis, collagen induced arthritis, and systemic lupus. Blockade of CD40: CD40L binding appears to reduce the ability of macrophages to produce nitric oxide, which mediates many of the macrophages' pro-inflammatory activities.

It appears from such studies that blocking CD40:CD40L interactions and/or blocking of CD28:CD80 or CD28:CD86 interactions can modulate immune responses.

Immunohistochemical data (Example 2) was shown to correlate well with the gene expression data and these data identify macrophages as an antigen presenting cell infiltrating skeletal muscle during disease progression in the G93A mouse.

Because the genetic expression data indicated the involvement of the co-stimulator pathway, the efficacy of MRI was evaluated in the G93A model. MR1 binds to CD40L thus blocking its interaction of CD40 which participates in the co-stimulatory pathway involved in an immune response. It has been reported in the literature that MR1 is efficacious for the treatment of rheumatoid arthritis and graft versus host disease both of which have a strong immunologic component. Rheumatoid arthritis is an autoimmune disease and graft versus host disease arises when the host's body mounts a vigorous immune response against the graft tissue.

Although ALS has an immune component mediated by activation of microglia and astrocytes it is not considered to be an autoimmune disorder. Several anti-inflammatory drugs failed to show efficacy in preclinical or clinical testing including TNFα-inhibitors, Celebrex®, minocycline, and thalidomide. It was thus unexpected to find that MR1, showed efficacy in the G93A ALS model.

Methods according to the present disclosure include methods of treating a patient with a neurodegenerative and/or a neuromuscular disorder by administering to the patient a compound that blocks the interaction of CD40L and CD40 and/or blocks the interaction of CD28 and CD80 and/or blocks the interaction of CD28 and CD86. One embodiment is a method of treating a patient having Alzheimer's Disease, Parkinson's Disease, Amyotrophic Lateral Sclerosis, Myasthenia Gravis, Multifocal Motor Neuropathy, Primary Lateral Sclerosis, Spinal Muscular Atrophy, Kennedy's Disease, and Spinocerebellar Ataxia by administering to the patient a compound that blocks the interaction of CD40L and CD40. In another embodiment the method of treating a patient is by administering an anti-CD40L antibody.

Therapeutic compounds useful for the methods of the invention include any compound that blocks the interaction of CD40 with CD40L. For example a number of animal studies describe agents capable of interrupting CD40:CD40L binding (see for example US2005158314 and U.S. Pat. No. 7,173, 046 which are hereby incorporated by reference.) And for example, numerous anti-CD40L antibodies have been produced and characterized. (see, e.g., U.S. Pat. No. 5,876,950) to Bristol-Myers Squibb, which is hereby incorporated by reference). Anti-CD40L antibodies useful in the methods of the present disclosure include, but are not limited to, MR1, a hamster monoclonal antibody available from Taconic (Hudson, N.Y.) and BD Biosciences (San Jose, Calif.); 5c8, a humanized antibody described in U.S. Pat. No. 5,474,771 (which is hereby incorporated by reference); a hamster human chimeric antibody, IDEC 131/E6040 is a humanized monoclonal antibody comprising human gamma-1 heavy chains and human kappa-light chains with CDRs of murine monoclonal antibody clone 24-31, commercially available from Ancell (catalog X 353-020, Bayport, Minn.); ABI 793; Sgn-40; ImxM90 (Immunex); ImxM91 (Immunex); ImxM92 (Immunex); and an anti-CD40L mAb commercially available from Genzyme (Cambridge, Mass., catalog No. 80-3703-01). Also commercially available is an anti-CD40L mAb from PharMingen (San Diego, Catalog #33580D). Embodiments according to the disclosure include methods of treating a patient with a neurodegenerative or neuromuscular disorder, comprises administering a therapeutically effective amount of an anti-CD40L antibody. One embodiment is a method of treating a patient with a neurodegenerative or neuromuscular disorder, comprising administering a therapeutically effective amount of an anti-CD40L antibody selected from MR1, 5c8, IDEC 131/E6040, clone 24-31, ABI 793, ImxM90, ImxM91, ImxM92, or Sgn-40. In one embodiment the antibody is 5c8. In another embodiment the antibody is MR1.

In some embodiments the neurodegenerative or neuromuscular disorder is Alzheimer's Disease, Parkinson's Disease, Amyotrophic Lateral Sclerosis, Myasthenia Gravis, Multifocal Motor Neuropathy, Primary Lateral Sclerosis, Spinal Muscular Atrophy, Kennedy's Disease, or Spinocerebellar Ataxia. One embodiment is a method of treating a patient with Amyotrophic Lateral Sclerosis comprising administering a therapeutically effective amount of an anti-CD40L antibody. In a particular embodiment the anti-CD40L antibody is MR1. In another particular embodiment the anti-CD40L antibody is 5c8.

In another embodiment the method of treatment comprises administering a therapeutically effective amount of an anti-CD40 antibody. In some embodiments the anti-CD40L compounds are Fab fragments, F(ab')$_2$, F(ab'), single chain antibodies, polypeptides, fusion constructs of polypeptides and the like. In some embodiments the compounds are small molecule compounds that are capable of blocking the CD40:CD40L interaction. In other embodiments these compounds include BIO3417, or any of the compounds disclosed in U.S. Pat. No. 7,173,046, having the ability to block the CD40:CD40L interaction.

The compounds that block the CD40:CD40L interaction may be administered in combination with other compounds. Thus, another embodiment is a method of treating a patient with a neurodegenerative or neuromuscular disorder comprising administering a compound that blocks the interaction of CD40L and CD40 in combination with a compound that blocks the interaction between CD80 and CD28. Another embodiment is a method of treating a patient by administering a compound that blocks the interaction of CD40L and CD40 in combination with a compound that blocks the interaction between CD86 and CD28. In one embodiment, the compound that blocks the interaction of CD80 and CD28 is galiximab, or H1f1 & h3d1, or 16C10, or 7C10. In one embodiment the compound that blocks the interaction between CD86 and CD28 is a CTLA4-Ig protein conjugate such as abetacept or belatacept. Embodiments according to the present disclosure also include a method of treating a patient with a neurodegenerative or neuromuscular disorder comprising administering a compound that blocks the interaction of CD40L and CD40 in combination with a compound that blocks the interaction between CD80 and CD28 or administering a therapeutically effective amount of a compound that blocks the interaction of CD40L and CD40 in combination with a compound that blocks the interaction between CD86 and CD28, wherein the neurodegenerative or neuromuscular disorder is Alzheimer's Disease, Parkinson's Disease, Amyotrophic Lateral Sclerosis, Myasthenia Gravis, Multifocal Motor Neuropathy, Primary Lateral Sclerosis, Spinal Muscular Atrophy, Kennedy's Disease, or Spinocerebellar Ataxia. In certain embodiments the compound that blocks the interaction of CD40L and CD40 is MR1 and the compound that blocks the interaction between CD28 and CD86 or between CD28 and CD80 is abatacept, galiximab or belatacept. In other embodiments, the compound that blocks the interaction of CD40L and CD40 is 5c8. Another embodiment is a method of treating a patient with Amyotrophic Lateral Sclerosis comprising administering a therapeutically effective amount of MR1 in combination with abatacept or belatacept. Another embodiment is a method of treating a patient with Amyotrophic Lateral Sclerosis comprising administering a therapeutically effective amount of 5c8 in combination with abatacept or belatacept.

V. Pharmaceutical Compositions and Methods of Administration

To treat any of the foregoing disorders, pharmaceutical compositions for use in accordance with the methods of the present disclosure may be formulated in a conventional manner using one or more physiologically acceptable carriers. Pharmaceutically acceptable carriers are determined in part by the particular composition being administered, as well as by the particular method used to administer the composition. Accordingly, there are a wide variety of suitable formulations of the compounds useful in the methods of the present disclosure (see, e.g., Remington: The Science and Practice of Pharmacy, 20th ed., Gennaro et al. Eds., Lippincott Williams and Wilkins, 2000).

Formulations suitable for oral administration include, for example, solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives.

According to the present disclosure the compounds can be administered by any suitable means, which can vary, depending on the type of disorder being treated and on the nature of the compound itself. For example the compounds may be administered orally, parenterally or topically. For proteins such as antibodies, administration routes preferably include parenteral, e.g., intramuscular, intravenous, intraarterial, intraperitoneal, or subcutaneous. Preferably, the parenteral dosing is given by injection, most preferably intravenous, intramuscular or subcutaneous injection. The amount to be administered will depend on a variety of factors such as the clinical symptoms, weight of the individual, and whether other drugs are administered. It should be appreciated that determination of proper dosage forms, dosage amounts, and routes of administration is within the level of ordinary skill in the pharmaceutical and medical arts, and is described below.

VI. Examples

Example 1

Characterization of the Molecular Mechanisms of Neurodegeneration in the G93A Mouse Model of ALS In order to identify molecular pathways amenable to therapeutic development, changes in gene expression patterns were characterized during disease progression in the G93A mouse model. Whole genome transcriptional profiling was studied using Affymetrix GeneChip® Mouse Expression set 430vII MOE430vII genechips. A longitudinal study design was employed comparing G93A skeletal muscle and spinal cord to non-transgenic littermates. In the G93A mouse model symptom onset is first seen as tail paralysis starting at approximately day 75 with progressive paralysis in the hindlimbs, then forelimbs, and finally diaphragm. The mean survival of the G93A animal colony is 134 days. The longitudinal study design collected calf muscle (gastrocnemius muscle) and spinal cord from G93A animals and wild type litter mates at days 30, 50, 60, 80, 90, 100, 110, and 120 (day 0 is date of birth). For each time point, tissues were collected from 5 wild type and 5 G93A animals and processed independently for a total of 160 tissues.

Animals were euthanized according to IACUC protocols at the appropriate time points described above. Tissues were immediately harvested and snap frozen in liquid nitrogen. Frozen tissues were stored at −80 degrees Celsius. Total RNA was isolated simultaneously from the tissues using the Qiagen RNaEasy kit as described by the manufacturer. The isolated total RNA was amplified using standard T7 linear amplification incorporating a biotinylated nucleotide using the Ambion Message AMPII T7 in vitro transcription kit. Labeled probe was fragmented and hybridized to Affymetrix GeneChip® Mouse Expression set 430vII according to the manufacturer's protocol. Genechips were washed in Affymetrix GeneChip® Fluids Station 450 to remove non-hybridized probe. Genechips were scanned in an Affymetrix GeneChip® 3000 7G scanner.

All computational processing and modeling was performed using the R development language version 2.6 from Bioconductor. The spinal cord and gastrocnemius data sets were analyzed independently. Affymetrix CEL files were used for all data preprocessing. All the CEL files in each data set were quality controlled using the Bioconductor vignettes SIMPLE AFFY, AFFY and AFFY PLM. The statistical changes in gene expression between G93A and wild type tissues at a given time point were assessed using the LIMMA package. The bayes model was used to determine the significance of expression changes between groups.

Figure 1B:
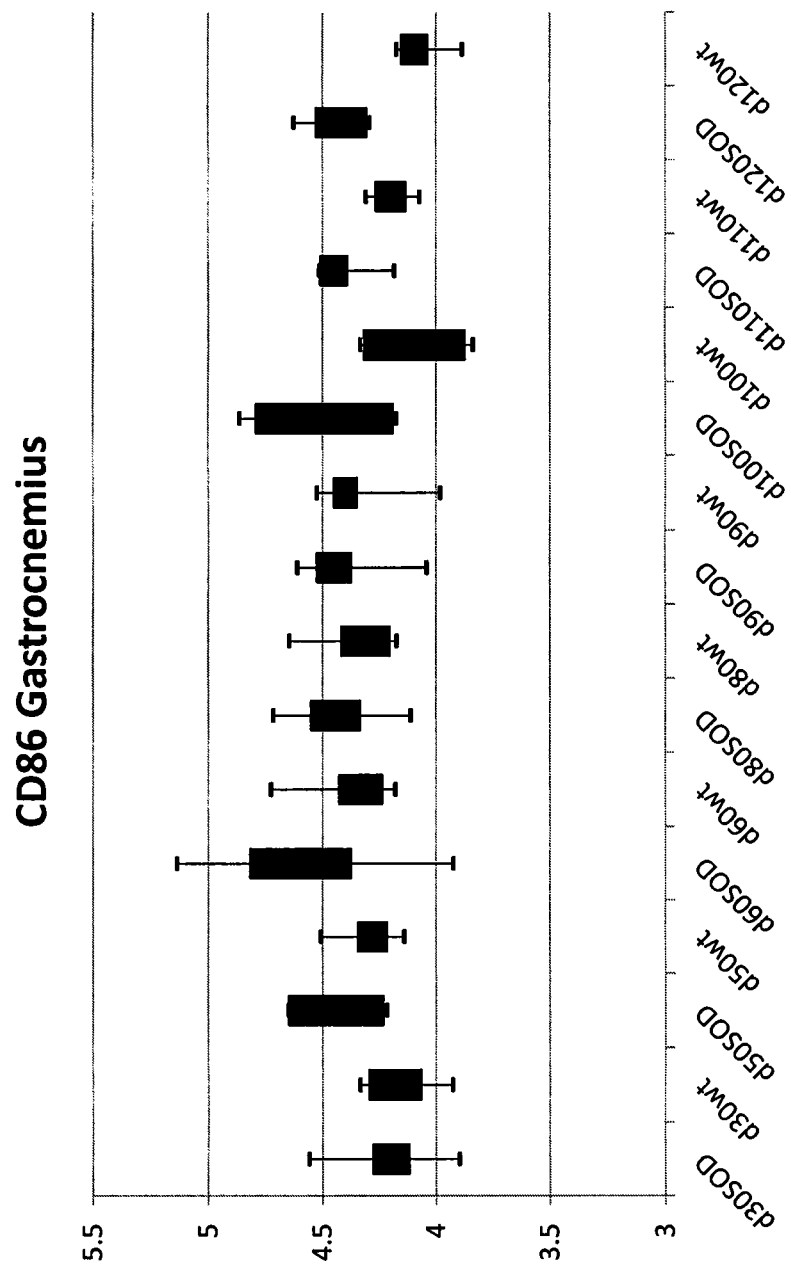
Figure 1C:
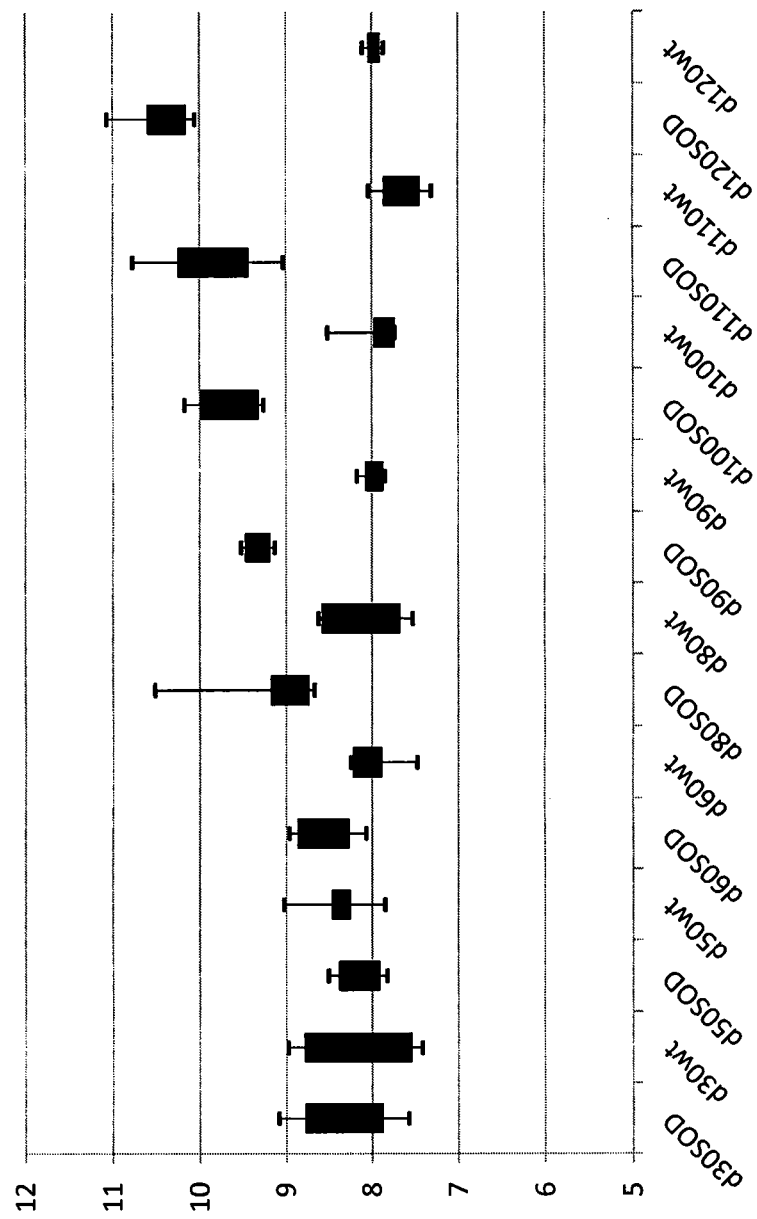
Figure 1D:
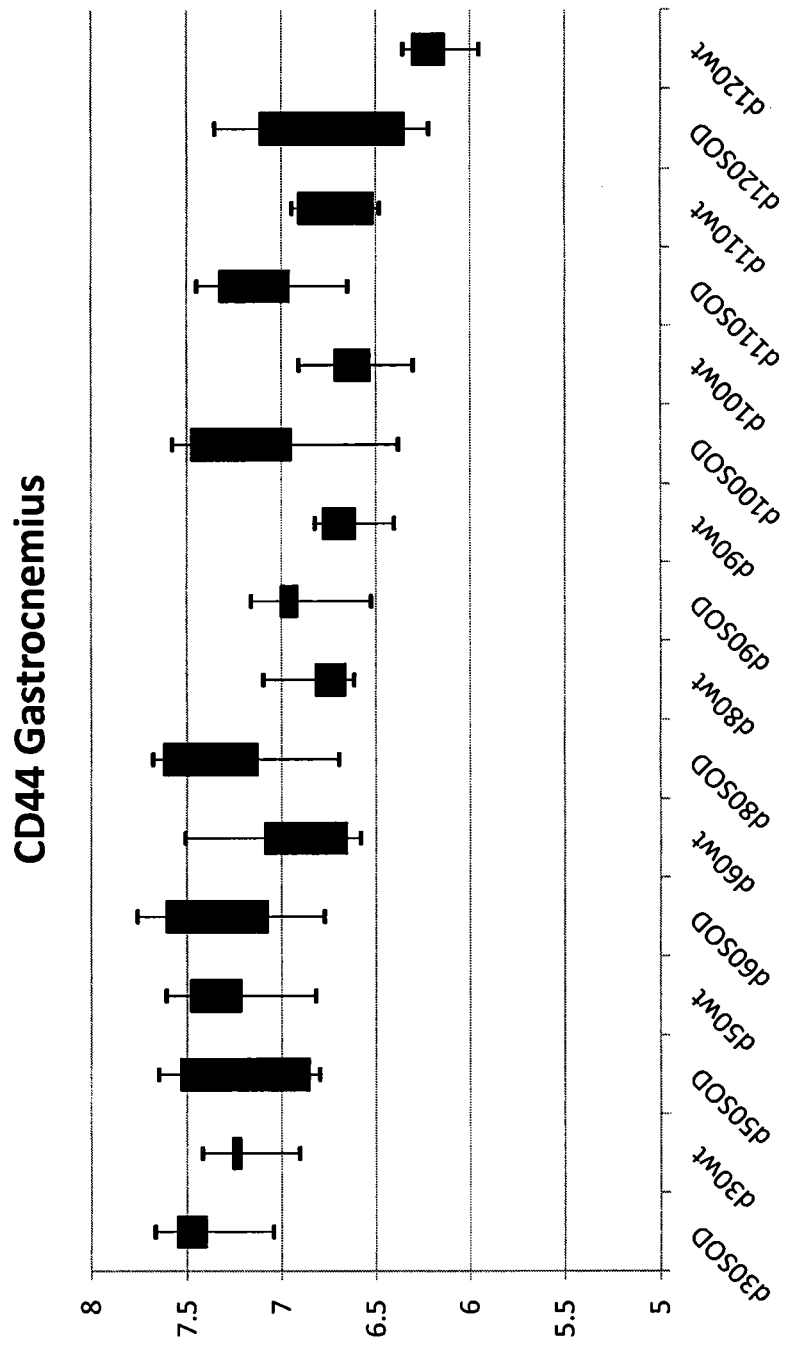
Figure 1E:
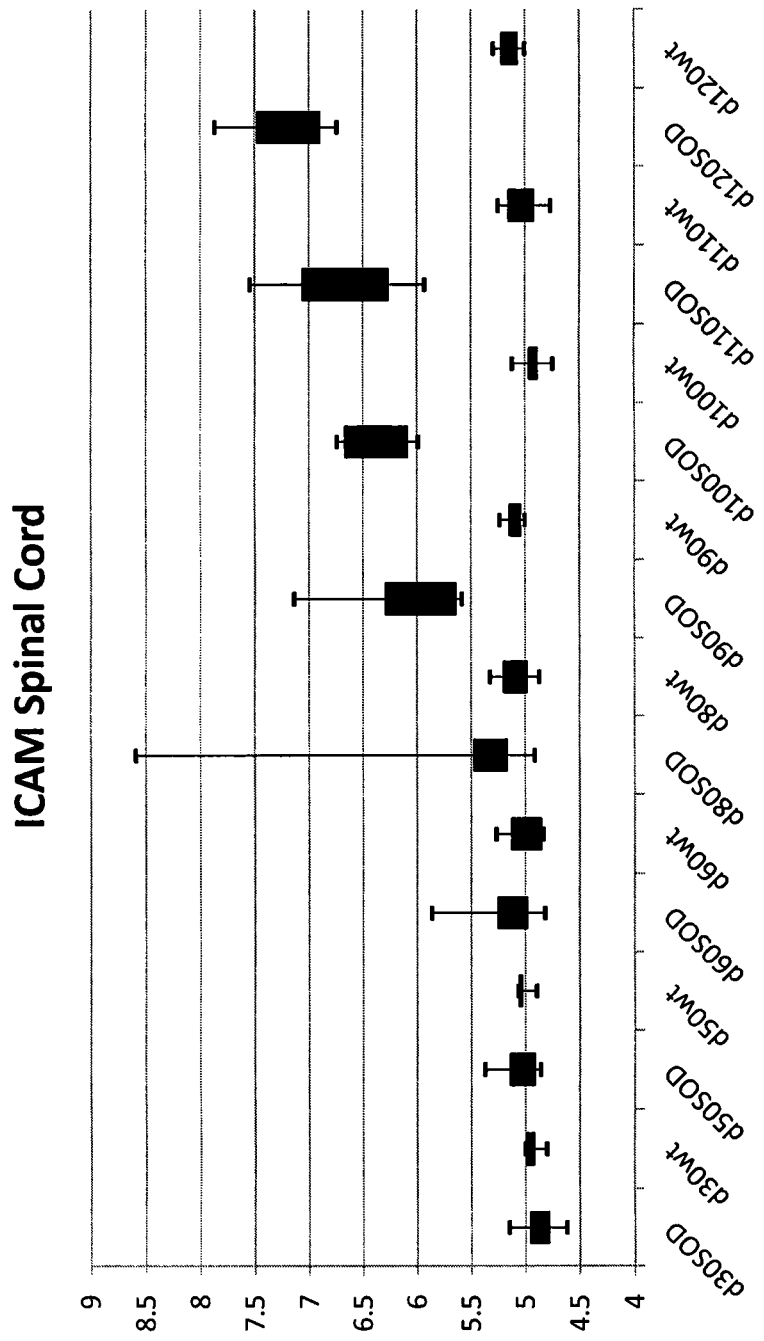
Figure 1F:
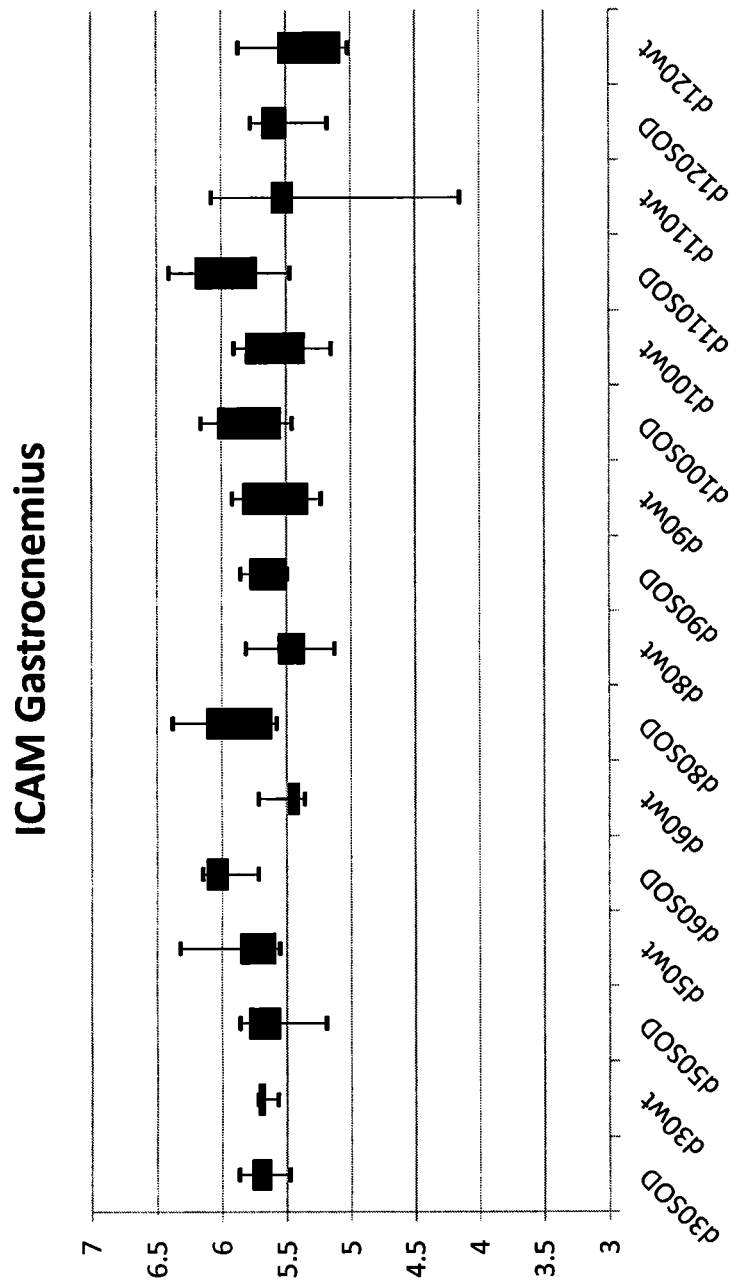
Figure 1G:
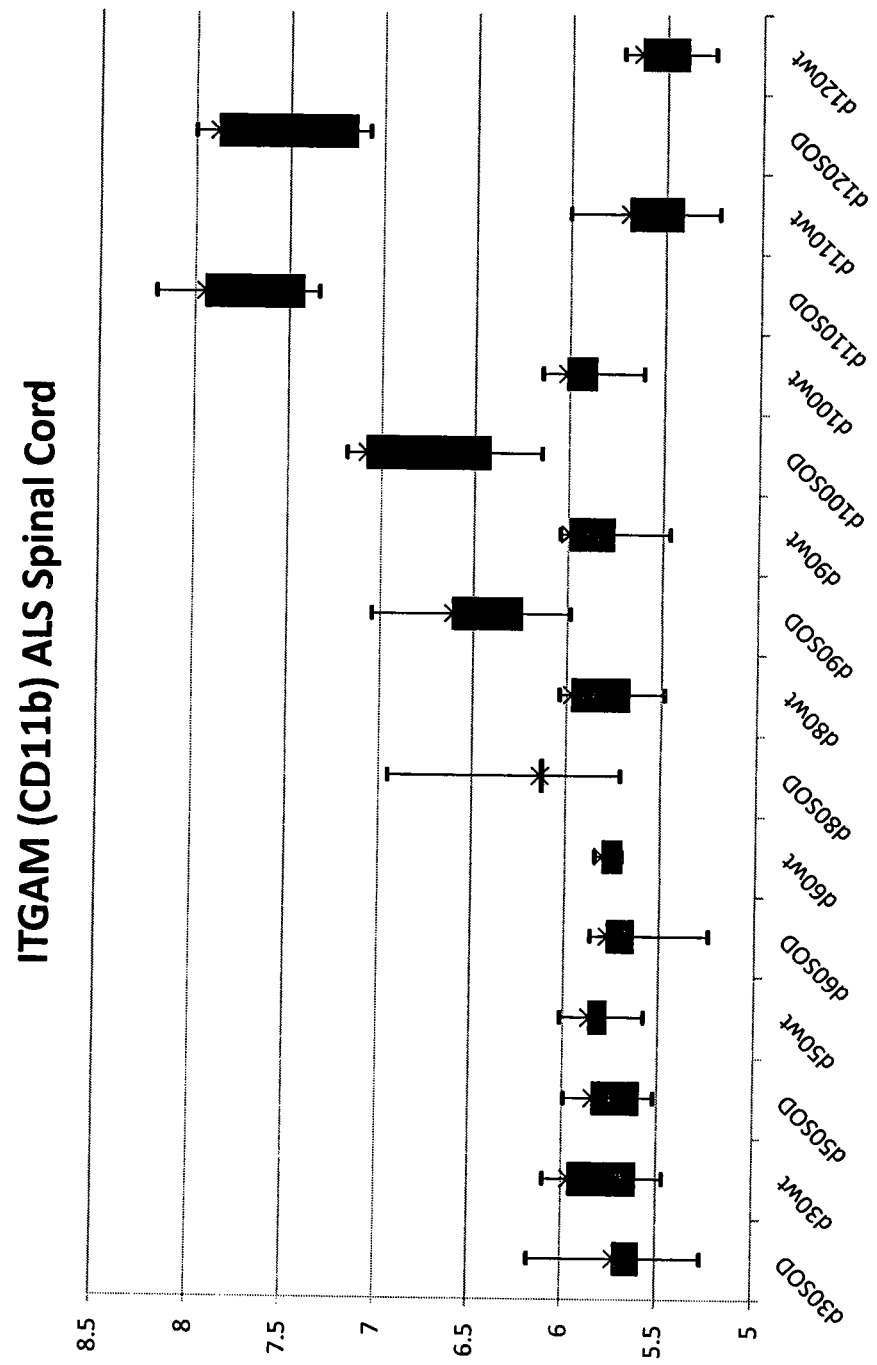
Figure 1H:
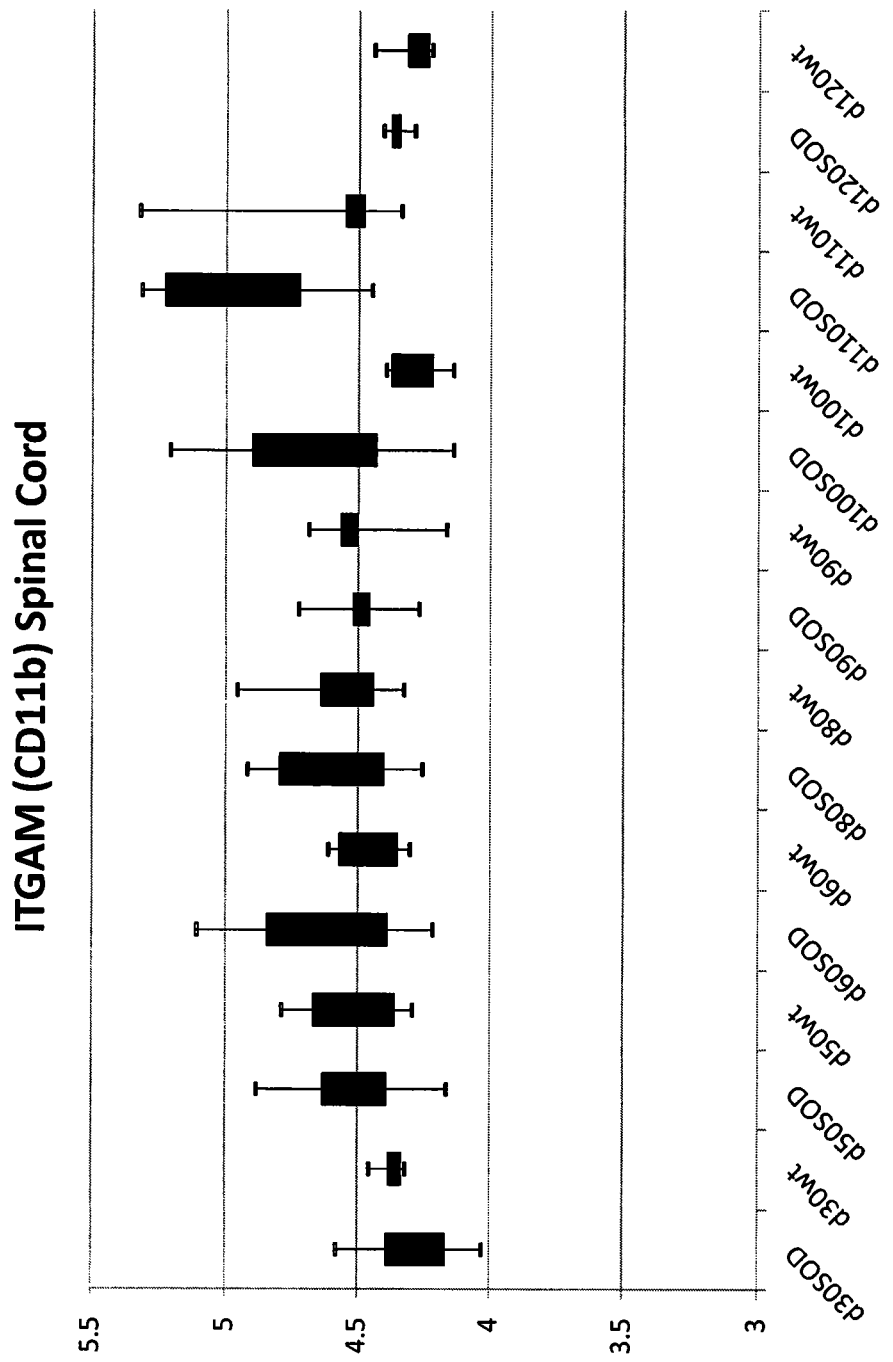
Figure 1I:
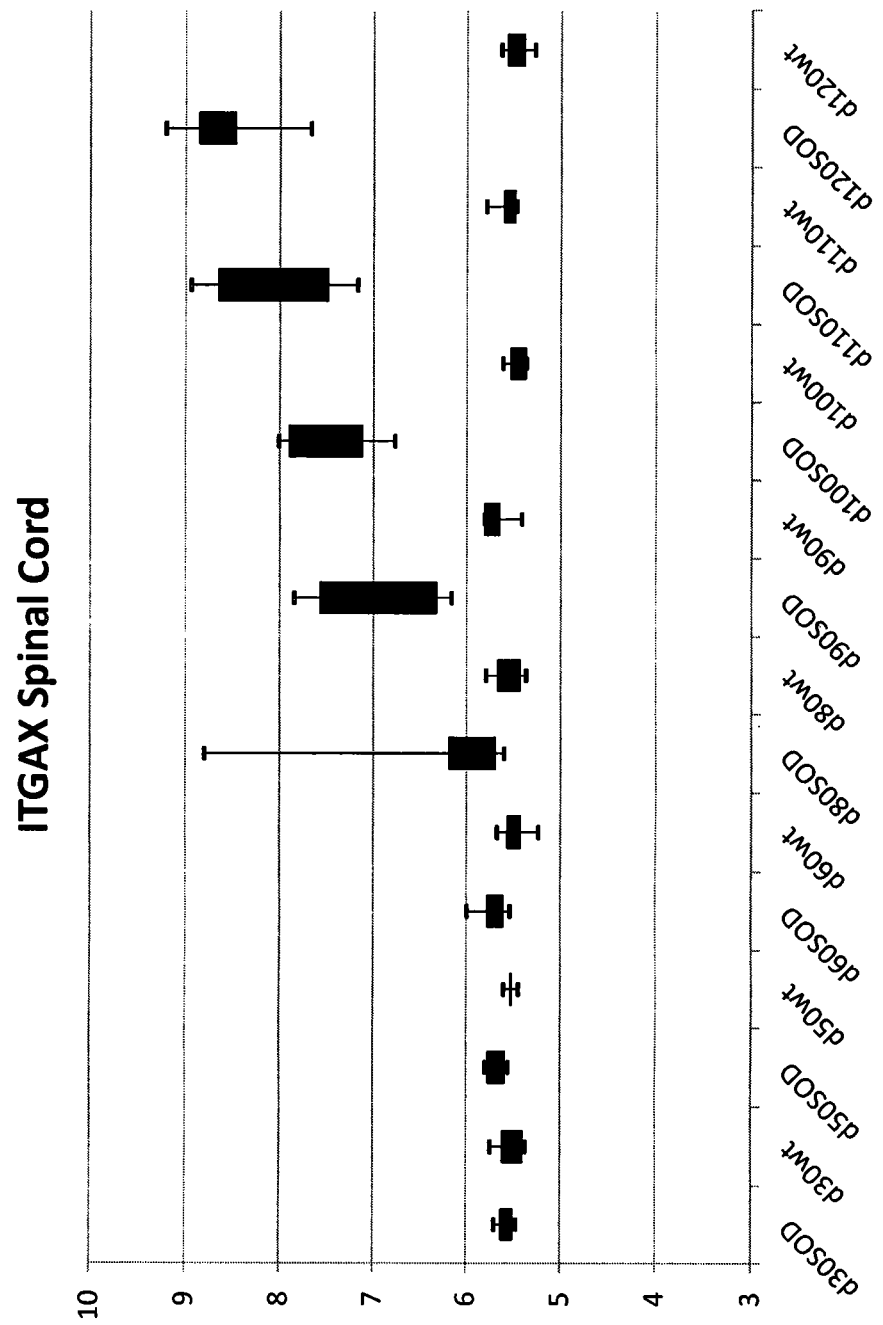
Figure 1J:
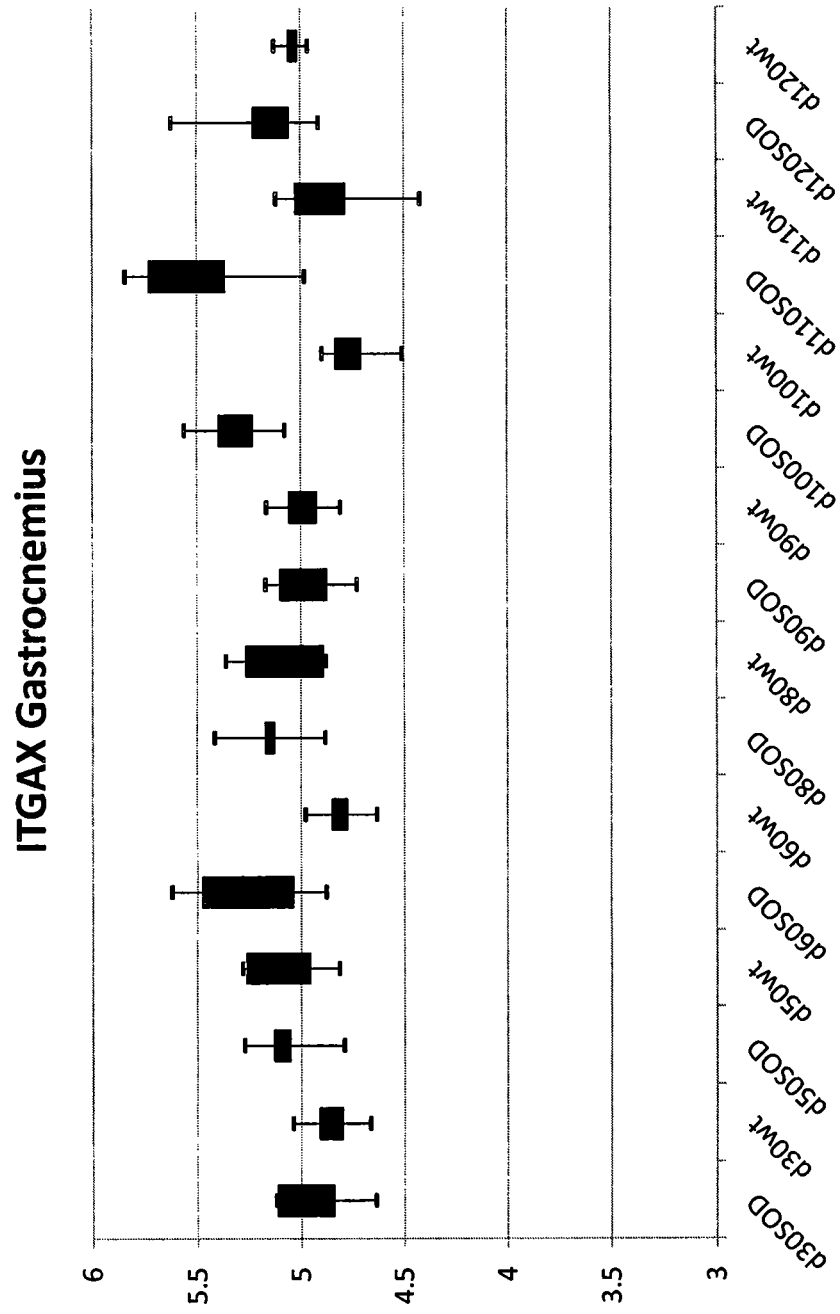
Figure 1K:
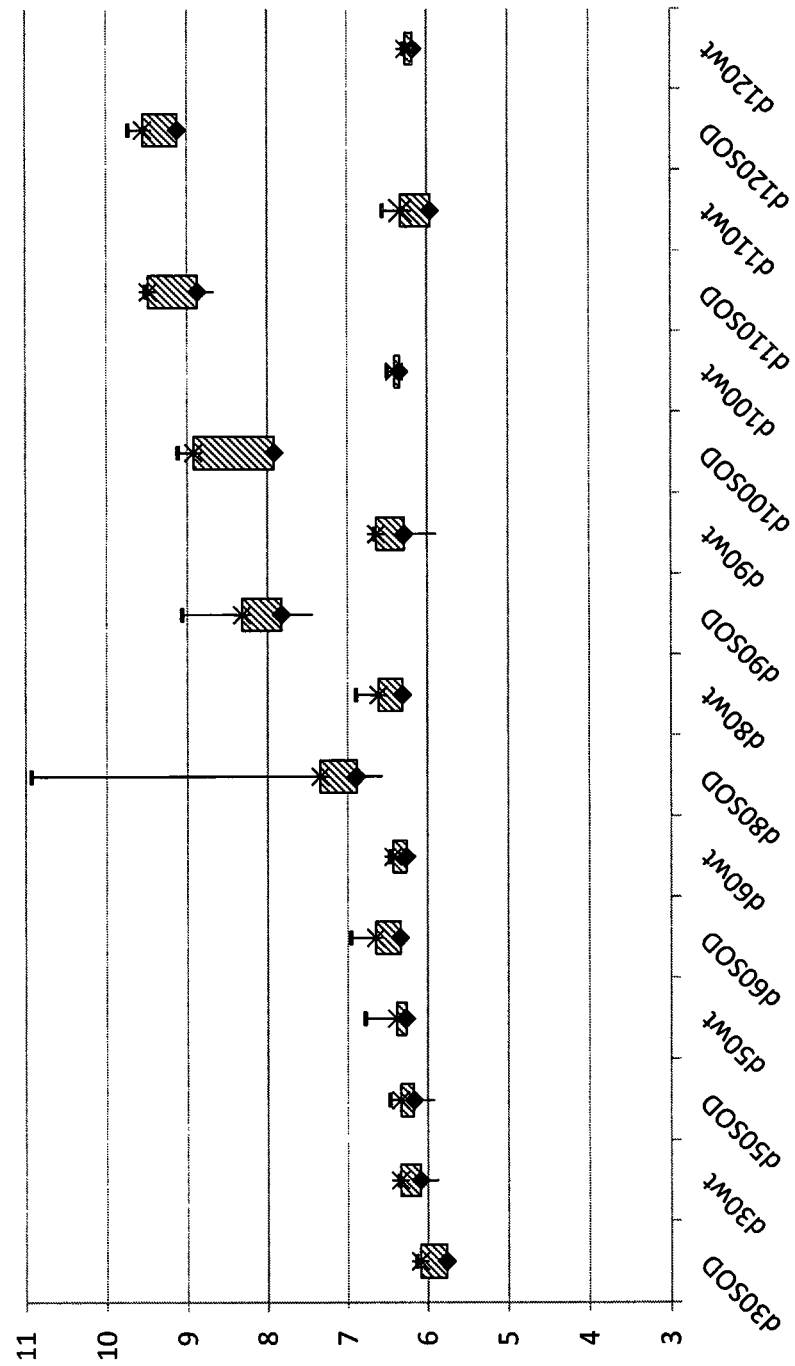
Figure 1M:
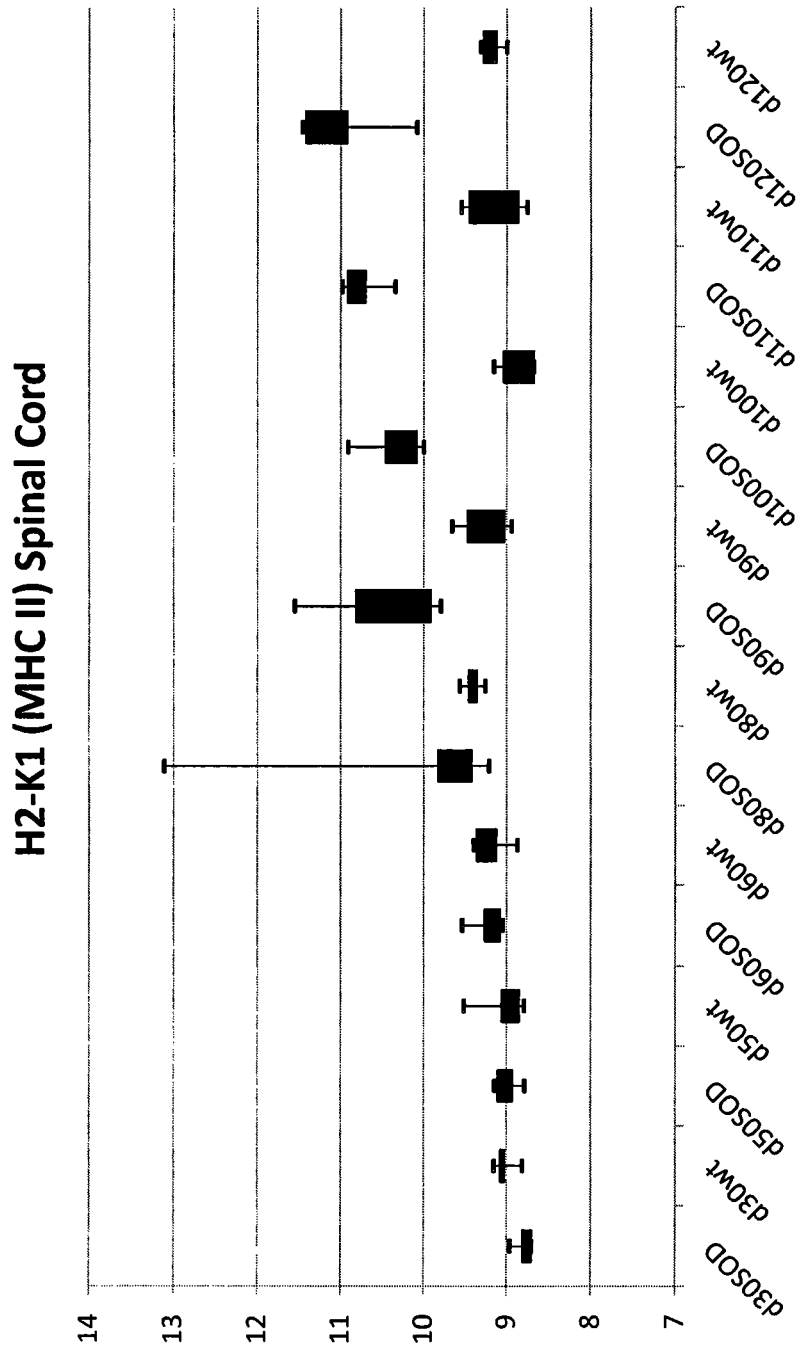
Figure 1N:
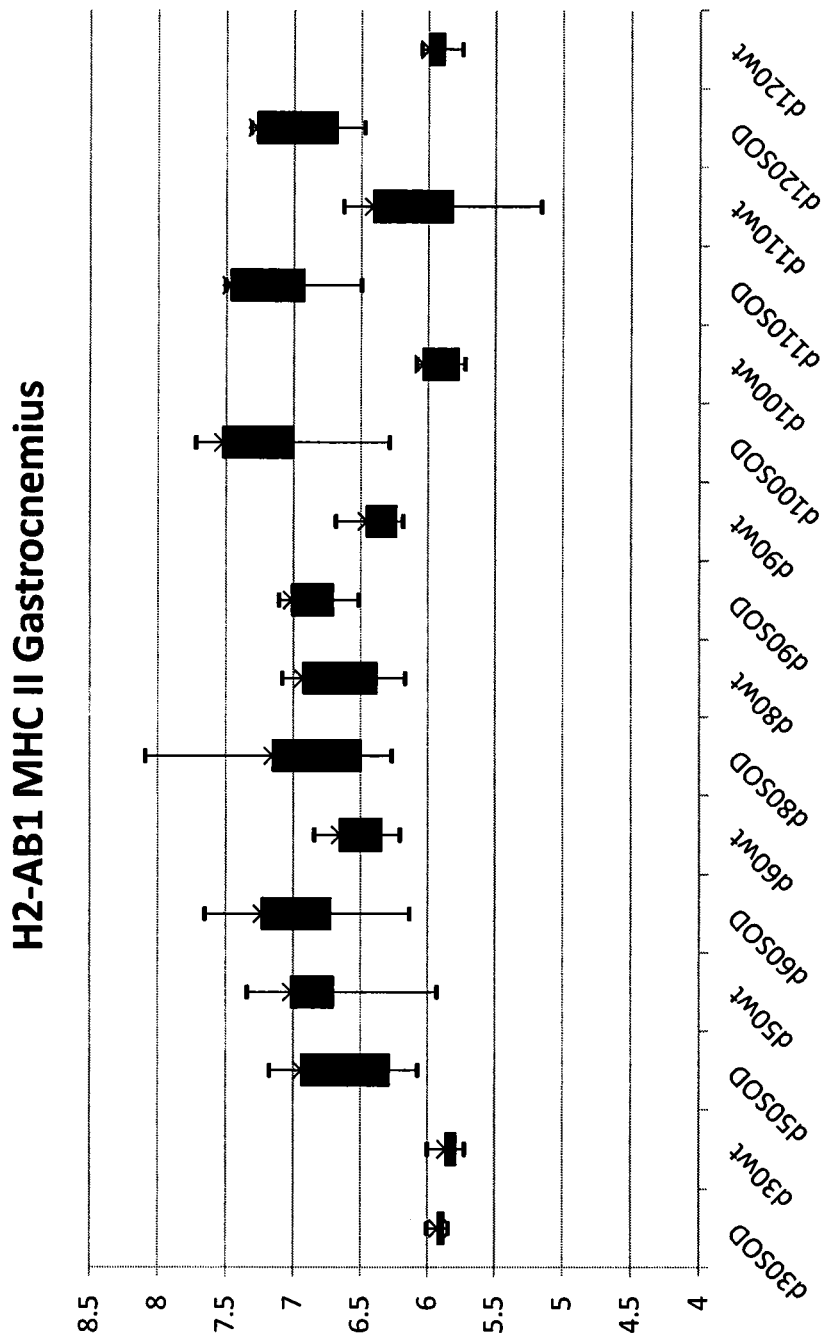
Figure 10:
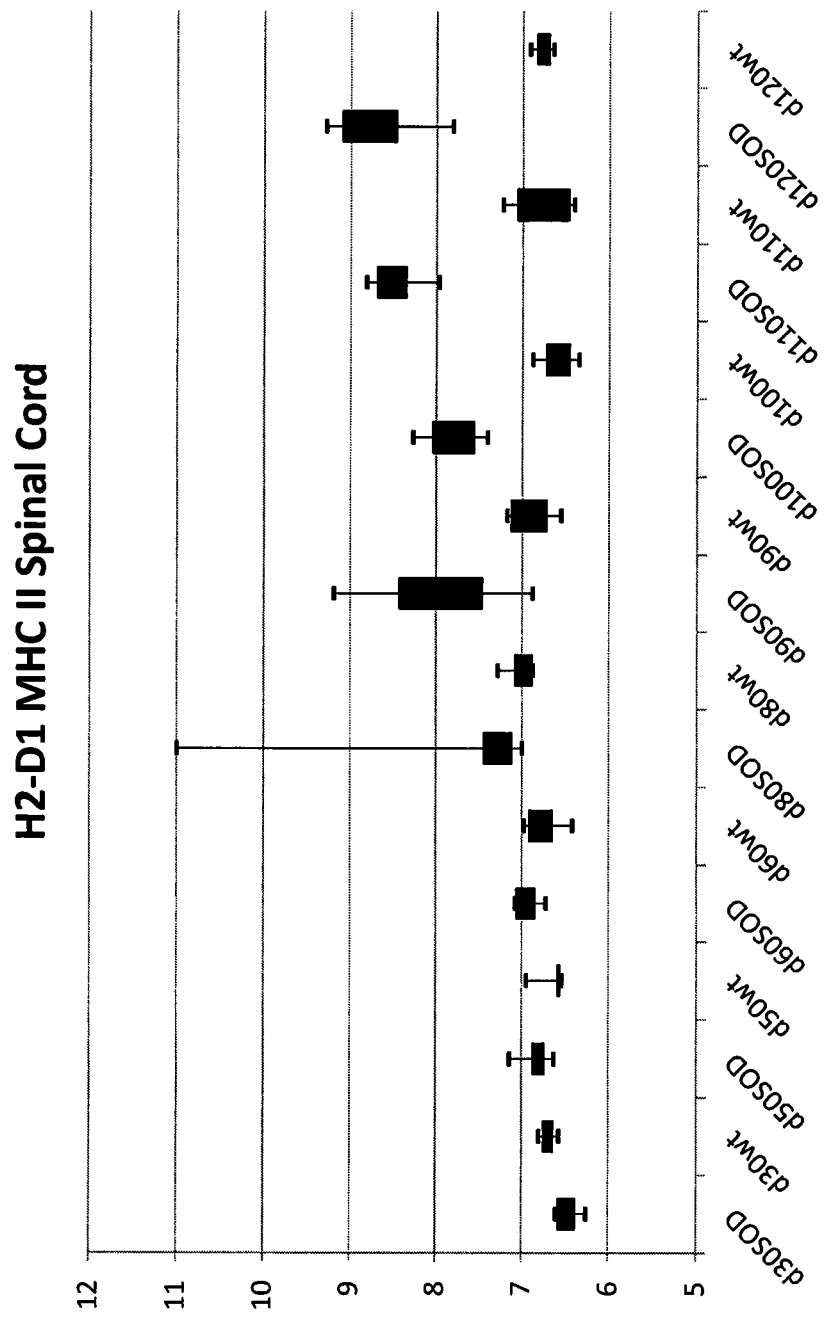

Genes that were found to be differentially expressed between the wild type and G93A animals include genes that are involved in the immune response and cell adhesion including CD86, CD44, ICAM, ITGAM, ITGA ITGAX, ITGB2, H2-K1 (MHC II), H2-AB1(MHC II), H2-D1 (MHCII), and H2-Eb1 (MHC II). The log 2 normalized expression profiles of these genes from wild type and G93A mice spinal cord and gastrocnemius at 30, 50, 60, 80, 90, 100, 110 and 120 days are shown in FIG. 1. FIGS. 1A and 1B show the differential expression of CD89 in spinal cord and gastrocnemius respectively. FIGS. 1C and 1D show the differential expression of CD44 in spinal cord and gastrocnemius respectively. FIGS. 1E and 1F show the differential expression of ICAM in spinal cord and gastrocnemius respectively. FIGS. 1G and 1H show the differential expression of ITGAM (CD11b) in spinal cord and gastrocnemius respectively. FIGS. 1I and 1J show the differential expression of ITGAX in spinal cord and gastrocnemius respectively. FIGS. 1K and 1L show the differential expression of ITGB2 in spinal cord and gastrocnemius respectively. FIG. 1M shows the differential expression of H2-K1 (MHC II) in spinal cord. FIG. 1N shows the differential expression of H2-AB1 (MHCII) in gastrocnemius. FIG. 1O shows the differential expression of H2-D1 (MHC II) in spinal cord. FIG. 1P shows the differential expression of H2-Eb1 (MHC II) in gastrocnemius.

These data show that inflammatory signatures increase during disease progression. These gene expression changes reflect the activation of antigen presenting cells such as dendritic cells, macrophages, and B cells. Blocking the interaction may ameliorate immune responses that exacerbate disease progression in ALS. The co-stimulatory pathway can be inhibited by blocking CD-28/CD80 or CD-28/CD86 or CD40/CD40L interactions.

Example 2

Characterization of Antigen Presenting Cells in Skeletal Muscle and the Peripheral Nervous System In order to determine the presence and localization of potential antigen presenting cells in gastrocnemius muscle from G93A and wild type animals, immunohistochemistry was performed on gastrocnemius tissues that were harvested from G93A and wildtype mice, at day 110. Immediately after harvesting, the tissues were embedded in OCT. Frozen sections were H&E stained and hybridized with antibodies to myelin (anti-S100b antibody) or antibodies to hematopoietic cell lineages including T cells (anti-CD3 antibody), B cells (CD45R pan B cell antibody), and macrophages (anti-CD11b antibody). At day 110 there was infiltration of CD11b positive macrophages and the macrophages appear to be localized to the axons of nerves innervating the skeletal muscle. The localization of macrophages is not dispersed across the entire muscle suggesting that the inflammation is not due to muscle atrophy or muscle fiber remodeling.

In order to confirm that identity of the monocyte lineage cells in the skeletal muscle at day 110 and to clarify the relevance of these cells compared to non-transgenic animals, additional immunohistochemistry was performed with a panel of antibodies specific for the macrophage lineage. An anti-S100b antibody was utilized to label the myelin associated axons innervating the skeletal muscle. All of the macrophage specific antibodies (anti-CD11b antibody, anti-CD86 antibody and anti-MAC1 antibody) localized macrophages to the axons of nerves innervating the skeletal muscle of G93A mice with no macrophages present on the axons of wildtype animals. The localization of macrophages was specific for nerves innervating the muscle with no macrophages present on myofibers in the muscle.

The gene expression data suggest that the genes associated with the co-stimulatory pathway are temporally increasing during disease progression both in spinal cord as well as in skeletal muscle (FIG. 1). In order to characterize the timing of macrophage infiltration into skeletal muscle immunohistochemistry was performed on gastrocnemius sections from days 60, 80, and 100 in G93A mice. There was no evidence of macrophage infiltration and localization to axons at day 60. Macrophages were evident at day 80 and localized to the axons innervating the muscle as described previously for skeletal muscle at day 110. The number of macrophages increased between day 80 and day 100 and accumulation of macrophages was specific to the axons innervating the skeletal muscle.

Figure 2:
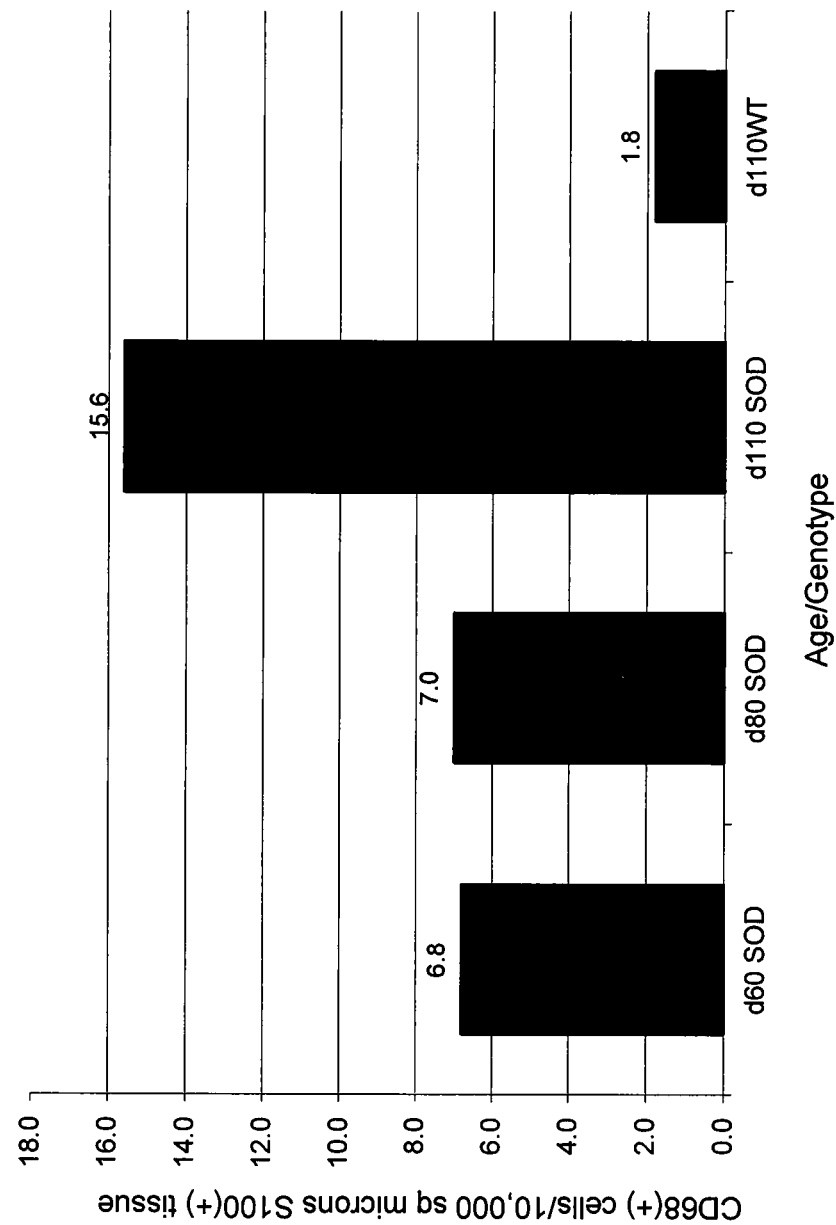
FIG. 2 shows the results of an analysis of macrophage of cell infiltration in gastrocnemius muscle from non transgenic and G93A mice at days 60 and 110.

In order to quantitate the increase in macrophage infiltration, representative sections from 5 G93A and 5 wild type animals were hybridized with anti-CD86 antibody and the number of macrophages per 10,000 square microns were counted. The number of macrophages in the wild type animals was the same at the 60, 80 and 110 day time points. As can be seen in FIG. 2 macrophages are accumulating in skeletal muscle temporally between days 80 and 100 and there are very few macrophages present in wild type skeletal muscle.

In summary, the immunohistochemical data correlates very well with the gene expression data and identify macrophages as the antigen presenting cell infiltrating skeletal muscle during disease progression in the G93A mouse model. An unexpected finding is that the macrophage infiltration appears to be specifically targeted to the axons innervating the skeletal muscle as localized by labeling with antibodies to myelin and macrophages.

Example 3

Pharmacokinetic Analysis of MR1 in G93A Tissues

Tissue levels of MR1 directed against murine CD40L were determined using a matrix matched, non-competitive enzyme linked immunoabsorbent assay (ELISA) in the sandwich format. Seven point standard curves were included on each plate. Standards were prepared using purified MR1 spiked into PBS diluent solution. PBS diluent solution was matrix matched with the normal mouse tissue at the equivalent dilution of the unknown samples to correct for any non-specific effects resulting from tissue lysates.

84 plasma samples were taken for pharmacokinetic analysis over a period of two weeks after dosing (10 mg/kg, IP) in both female and male G93A mice.

The elimination half-life was similar in females (23 d) and males (22 d) and similar to the half-life for a typical mouse IgG2-based antibody in the mouse. No signs of anti-hamster antibody response were seen.

Figure 3A:
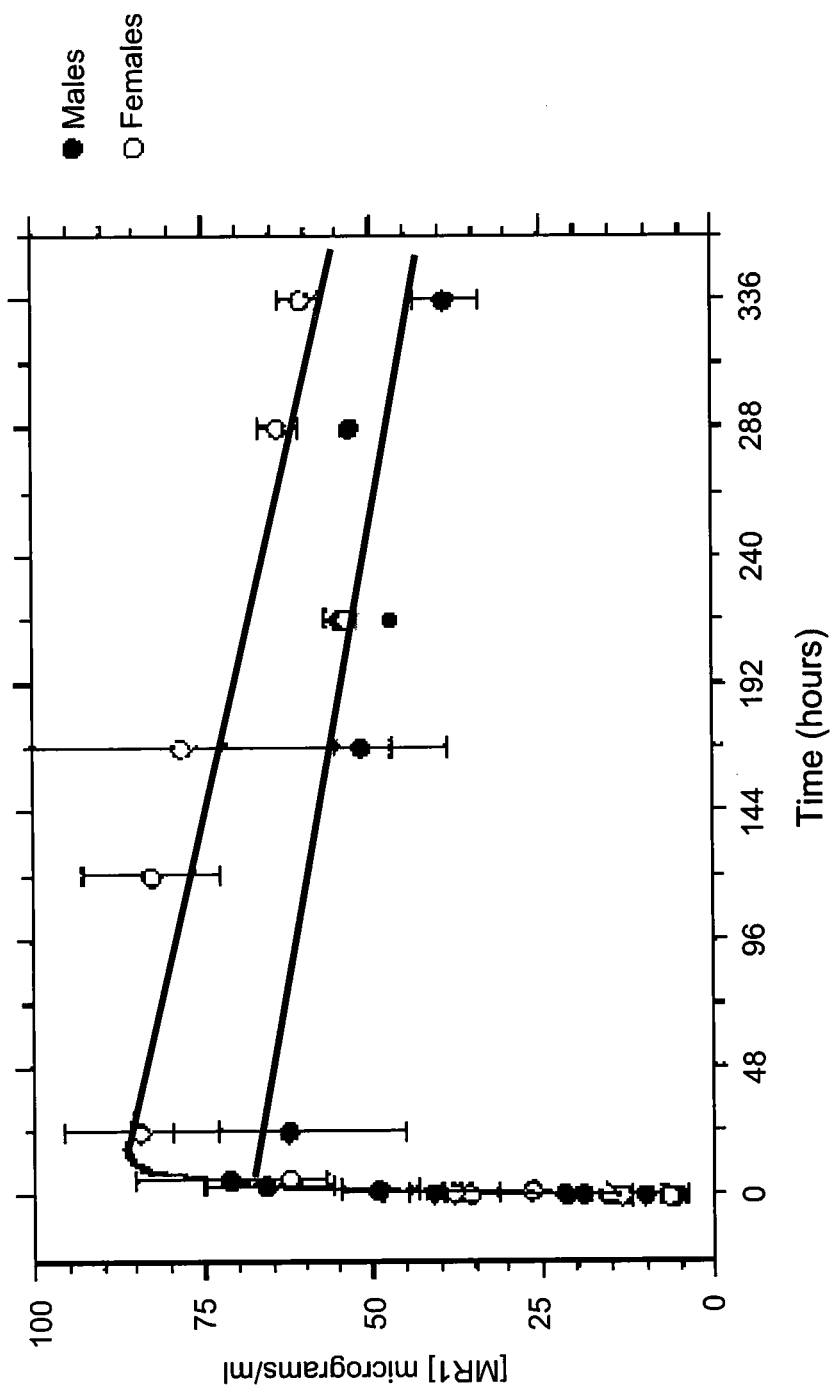
FIG. 3A shows MR1 concentration over time using a linear concentration (Y) axis.
Figure 3B:
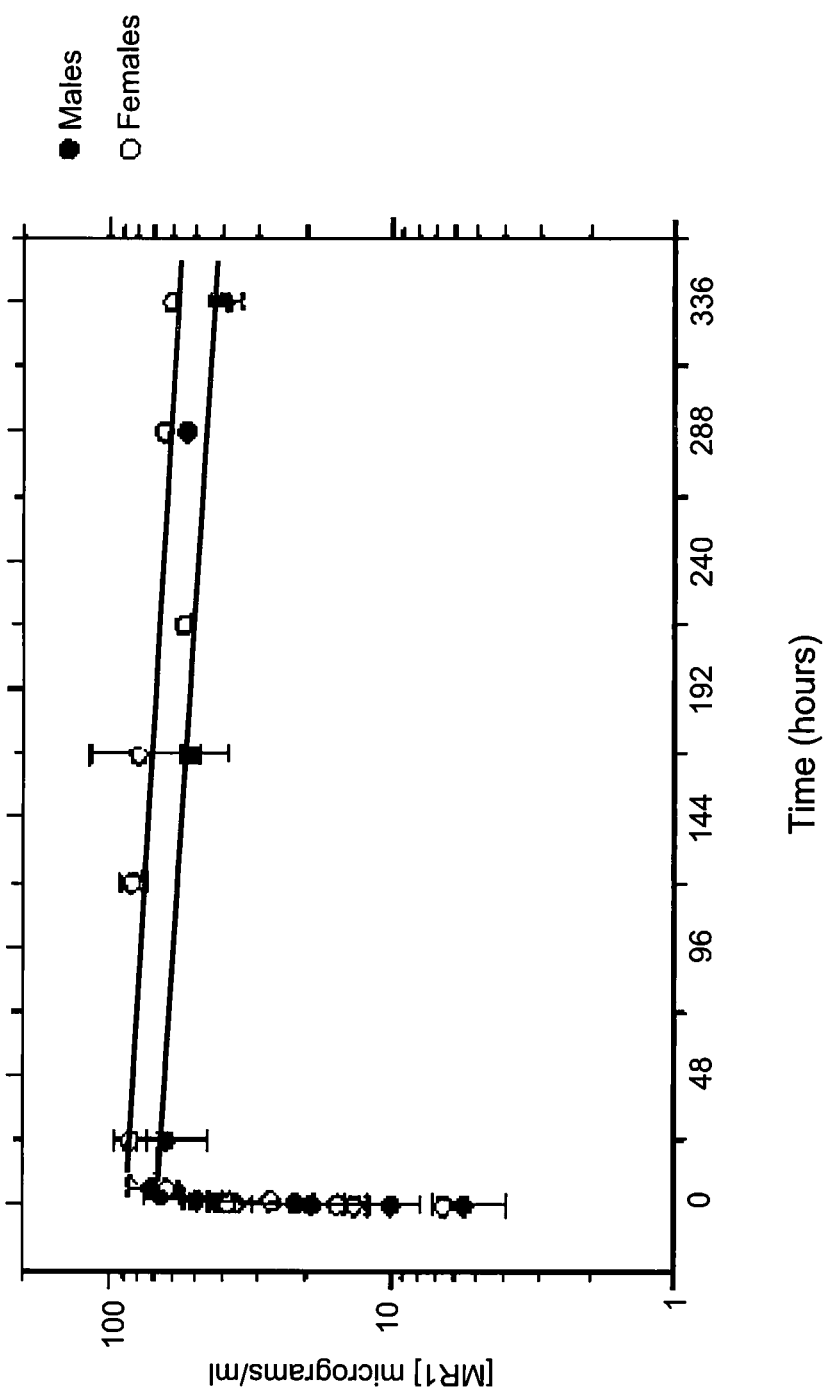
FIG. 3B shows MR1 concentration over time using a log concentration (Y) axis.

Females show a somewhat smaller volume of distribution for MR1 than males, and thus show higher plasma levels when given the same 10 mg/kg dose. Males show a faster clearance and higher volume of distribution. Thus, to attain similar plasma levels, males would require a higher dose. FIG. 3A shows MR1 concentration over time using a linear concentration (Y) axis. FIG. 38 shows MR1 concentration over time using a log concentration (Y) axis.

Example 4

MR1 Delays Disease Onset, Slows Disease Progression and Prolongs Survival in the G93A Mouse Model of ALS 36 female G93A mice were litter matched and randomized into two study groups. 18 G93A mice were placed into the MRI-treatment group and the other 18 G93A mice were placed into the control group. Study days are based on days from birth.

A single injection of 56 ug of MR1 was administered intraperitoneally (IP) on day 50. Subsequent to the bolus injection a weekly maintenance injection of 18 ug of MR1 was administered by IP injection. Doses were prepared in vehicle (phosphate buffered saline (PBS, pH 7.3)), to a total volume 200 µl. Control animals where administered 200 µl PBS. Beginning at day 54, animals were monitored daily throughout the course of the study and daily body weight measurements as well as neurological score were measured.

Neurological scores for both hind legs were assessed daily for each mouse from 50 days of age. The neurological score employed a scale of 0 to 4. (Scott et al., ALS Journal January 2008). Briefly animals assigned a score of 0 had full extension of hind legs away from lateral midline when mouse is suspended by its tail, and mouse can hold this for 2 seconds, suspended 2-3 times. Animals score a 1 when they display collapse or partial collapse of leg extension towards lateral midline (weakness) or trembling of hind legs during tail suspension. Animals score a 2 when the toes curl under at least twice during walking of 12 inches, or any part of foot is dragging along cage bottom/table. Animals score a 3 when they have rigid paralysis or minimal joint movement, or a foot not being used for forward motion. Animals score a 4 when they cannot right itself within 30 seconds from either side. If one hind leg is scored as 2, food pellets are left on bedding. If both hind legs are scored as 2, Nutra-Gel® (Bio-Serve #S4798) is provided as food in addition to food pellets on bedding and a long sipper tube is placed on the water bottle.

Date and cause of death were recorded for each mouse. For humane reasons, animals are closely monitored and sacrificed as moribund prior to actual death using criteria for severe moribundity. To determine duration of survival reliably and humanely, the moribund state, defined as the inability of mice to right themselves 30 seconds after being placed on a side (a neurological score of 4) was used. The moribund mice were scored as "dead", and were euthanized using carbon dioxide.

Standard procedure is to remove non ALS related deaths in both treatment and control groups prior to statistical analysis. In this case all animal deaths in either the control or treatment groups were attributed to ALS. Thus, no animals were censored due to non ALS related deaths.

Mutant SOD1 transgenic animals display normal body weight (SW) characteristics as neonates and gain weight normally compared to non-transgenic animals into adulthood. Depending on the nature of the genetic mutation in the transgene and the number of copies of mutant transgene weight loss becomes apparent in adult animals and continues until death. Analysis of weight loss in treatment and control groups can provide insight into putative treatment effects on disease onset and rate of progression. In order to assess the impact of MR1 treatment on body weight, two summary parameters are examined (1) Changes in BW from initiation of study to the attainment of peak body weight which may reflect an impact on disease onset (2) The changes in BW from peak body weight until death which may reflect an impact on disease progression.

Figure 4:
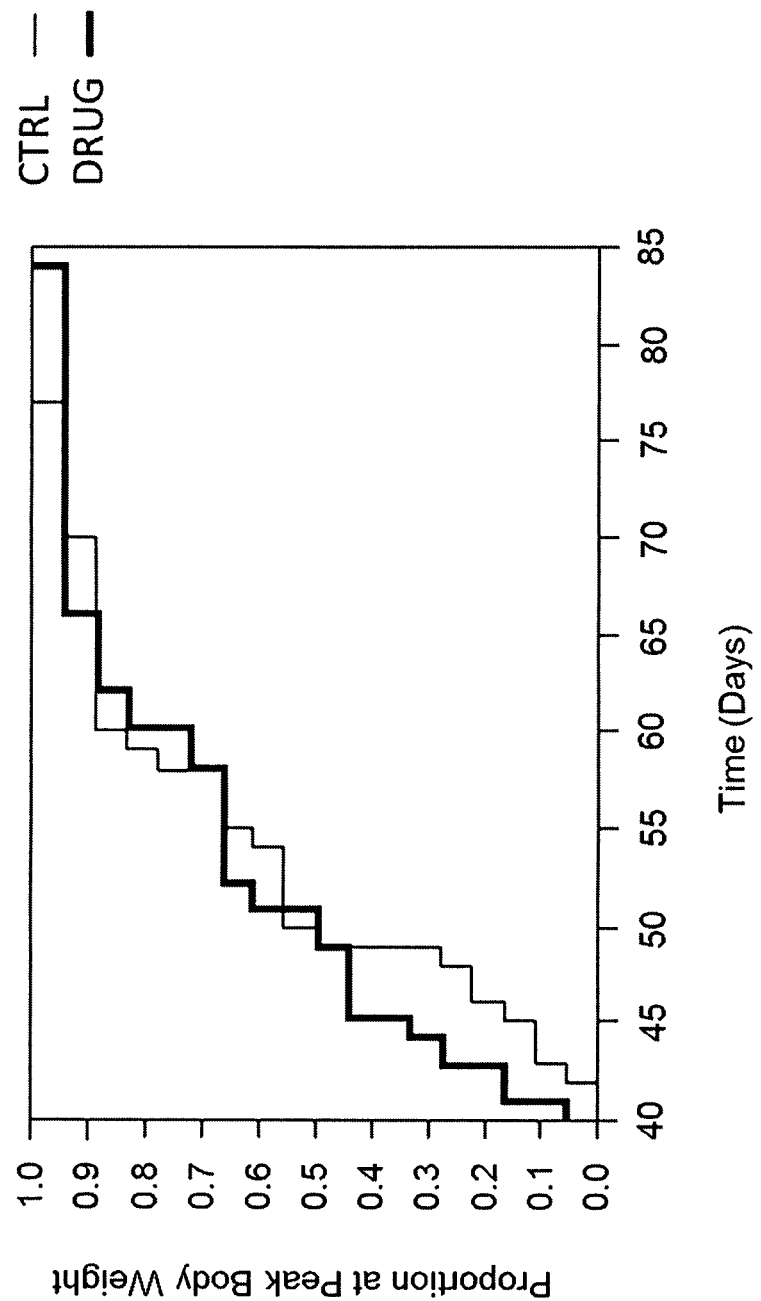
FIG. 4 is a graph of the mean daily body weight measurements starting at day 40 to attainment of peak body weight for the control and the treatment group.

Comparative MR1-treated and control group time-to-event curves for the time from day 40 to the attainment of peak body weight are shown in FIG. 4. The median time to peak body weight for the control group was 50 days compared to the MR1 treated group which was 51 days. This difference was not significant when analyzed by Kaplan Meier using the log rank and Wilcoxon statistical models, Cox proportional hazard, or parametric statistical tests.

Figure 5:
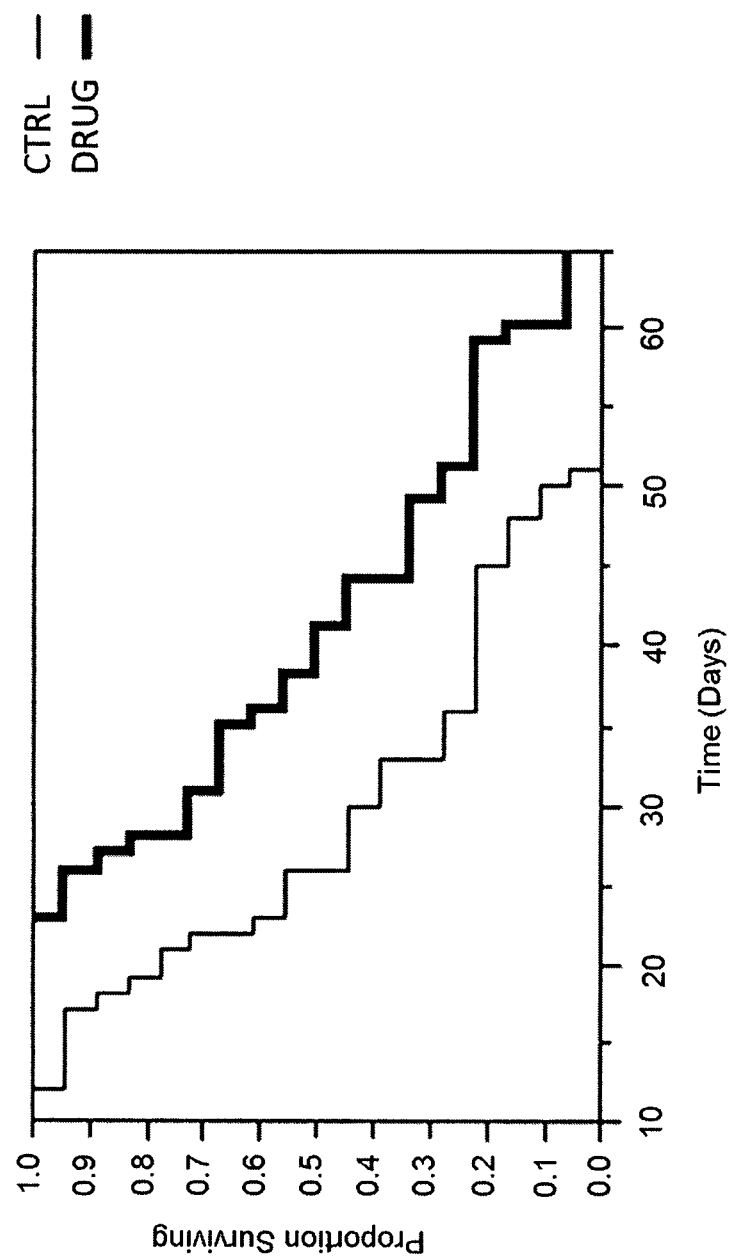
FIG. 5 depicts the mean daily body weight measurements from peak body weight to death for the control and treatment group.

Comparative MR1-treated and control group time-to-event curves for the time from peak body weight to death are shown in FIG. 5. Time from peak body weight to death was statistically significantly later by 15 days in MRI treated animals. Control animals have a 2.4 to 4.7-fold greater risk of dying sooner after attaining peak body weight than did MR1-treated animals. The median time from peak body weight to death in the control group was 26 days whereas in the MR1 treated group it was 41 days. Significance for each of the analyses in this example was calculated in several ways in order to better evaluate significance. The delay is statistically significant when analyzed using several approaches. (Kaplan Meier, log rank p=0.0110 and Wilcoxon, p=0.0069; Cox proportional Hazard model p=0.05151; parametric statistical model, p=0.0122). Based on the body weight data MR1 appears to have less of an impact on the onset of disease in the G93A mouse model but has a dramatic effect in slowing down the rate of body weight loss from peak body weight until death.

Figure 6:
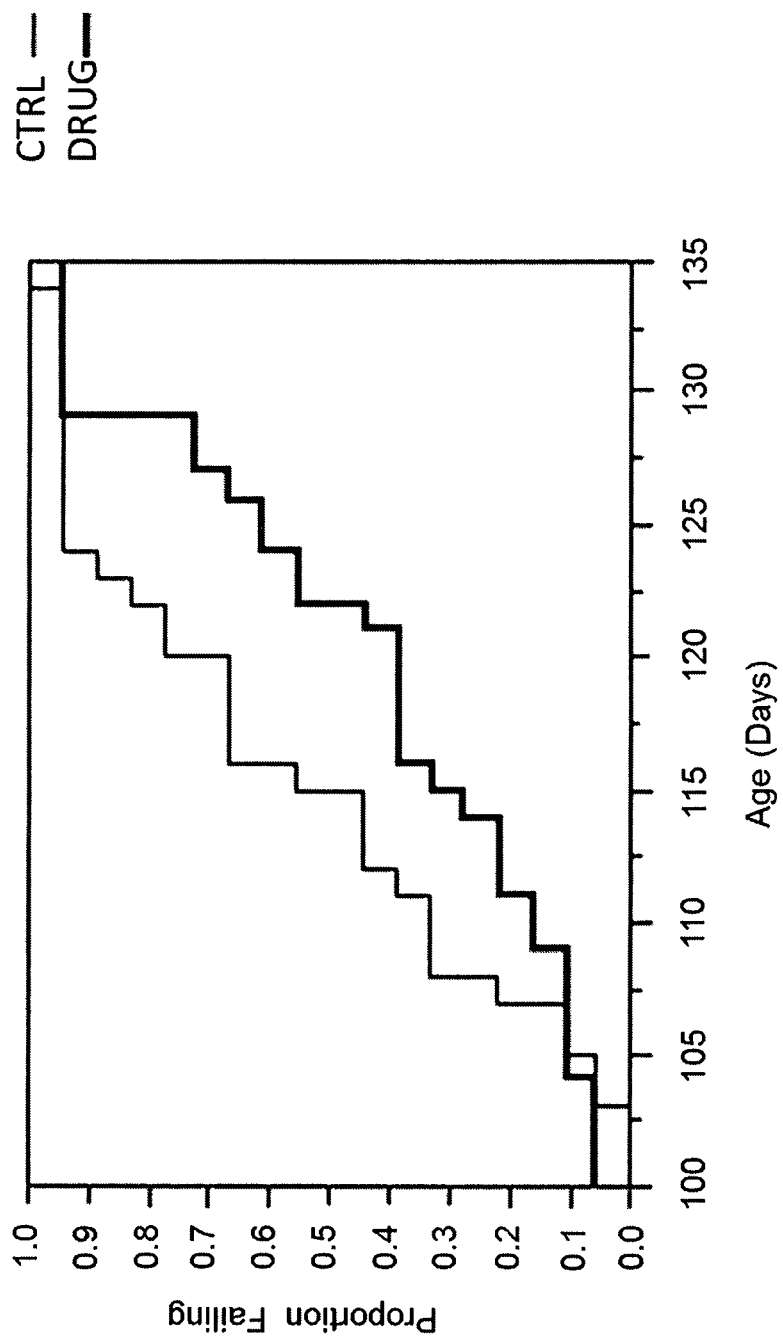
FIG. 6 depicts the time to disease onset based on the time to progress to a neurological score of 2 from the start of the study.
Figure 7:
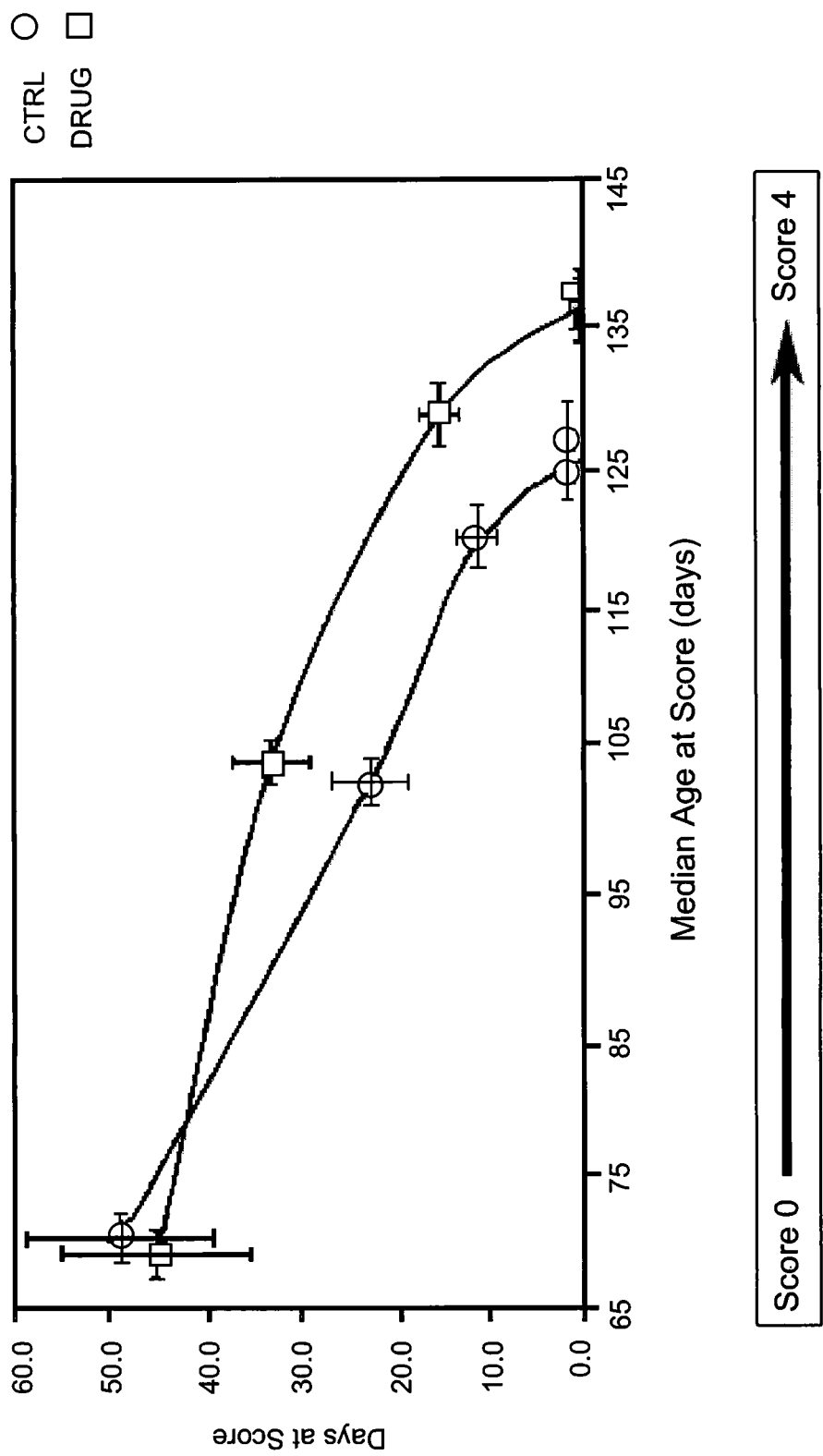
FIG. 7 is a graph representing the median age (X-axis) each group was at a given neurological score 0 to 4 as well as the number of days that each group was stable at a given score (Y-axis)

The timing of disease onset was also characterized by analyzing the daily neurological scores of the saline treated and MR1 treated groups. At the start of the study (day 50), all animals have a neurological score of 0 with no observable symptoms or paralysis. Disease onset can be characterized by examining the progression in neurological score from a neurological score of 0 to a neurological score of 2 when animals are clearly dragging a hind limb. The time-to-event plot for the age at which MR1 and control group animals progressed to a neurological score of 2 and the number of days at a neurological score of 2 is shown in FIG. 6. The median time at a neurological score of 2 for each group is plotted in FIG. 7. The time to attain a score of 2 in the control group is 115 days and for the MR1 treated group is 122 days. Based on the neurological score data MR1 delays disease onset in the G93A mouse model by approximately 7 days and the delay is statistically significant when analyzed using several approaches. (Kaplan Meier, log rank (p=0.0378) and Wilcoxon, (p=0.0591); Cox proportional hazard model, (p=0.0521); parametric analysis, (p=0.0582)). Days spent at each neurological score level is plotted against the median age at that score level in FIG. 7.

Figure 8:
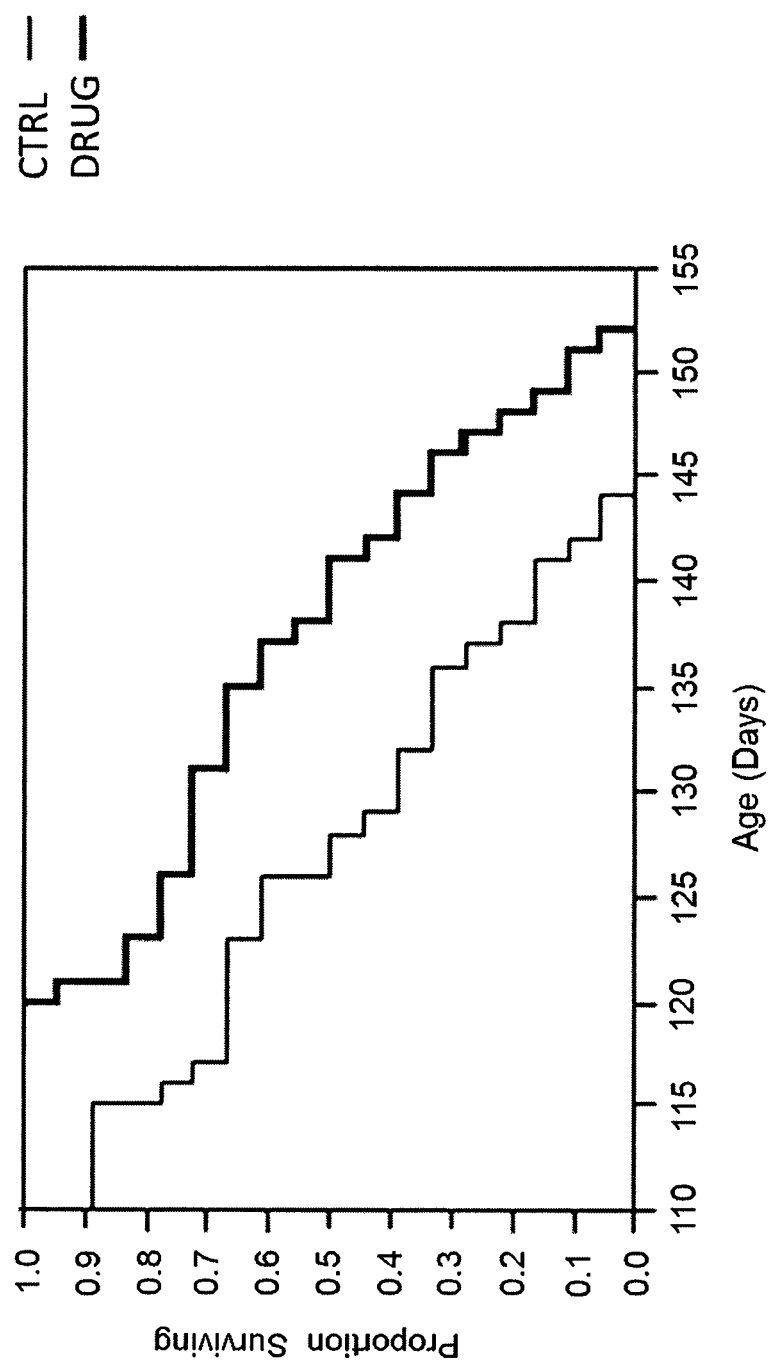
FIG. 8 shows a Kaplan Meier Survival Plot for the control and treatment group as calculated by a Cox proportional hazard model.

Treated animals survival time was later by 13 days than control animals. Comparative MR1-treated and control group time-to-event curves for the time from peak body weight to death are shown in FIG. 8. The median survival time for the control group was 128 days and the median survival for the MR1 treated group was 141 days. Control animals had a 2.8 to 3.2-fold greater risk of dying sooner than did MR1 treated animals. The delay is statistically significant when analyzed using several approaches. (Kaplan Meier, log rank (p=0.0040) and Wilcoxon test (p=0.0109); Cox proportional hazard model (p=0.0060); parametric analysis, (p=0.0049)).

Example 5

Optimized Dosing and Meta Analysis Demonstrate that MR1 Treatment Delays Disease Onset and Improves Survival in SOD1G93 Mice 60 female and 36 male G93A mice were litter matched and randomly assigned to treatment or control groups. 30 of the female and 18 of the male mice were treated with MR1 starting at day 50. Study days are based on birth.

A single bolus injection of 5.22 mg/kg or 6.75 mg/kg of MR1 was administered intraperitoneally at day 50 in females or males respectively. Subsequent to the bolus injection, females received weekly injections of ling/kg of MR1 and males received weekly injections of 1.34 mg/kg of MR1 via IP injection. Doses were prepared in vehicle (phosphate buffered saline (PBS, pH 7.3)), to a total volume of 200 μl. Control animals where administered 200 μl PBS. Animals were monitored for body weight, neurological score, non-related ALS deaths, and criteria for euthanization as previously described.

Figures 9A, 9B:
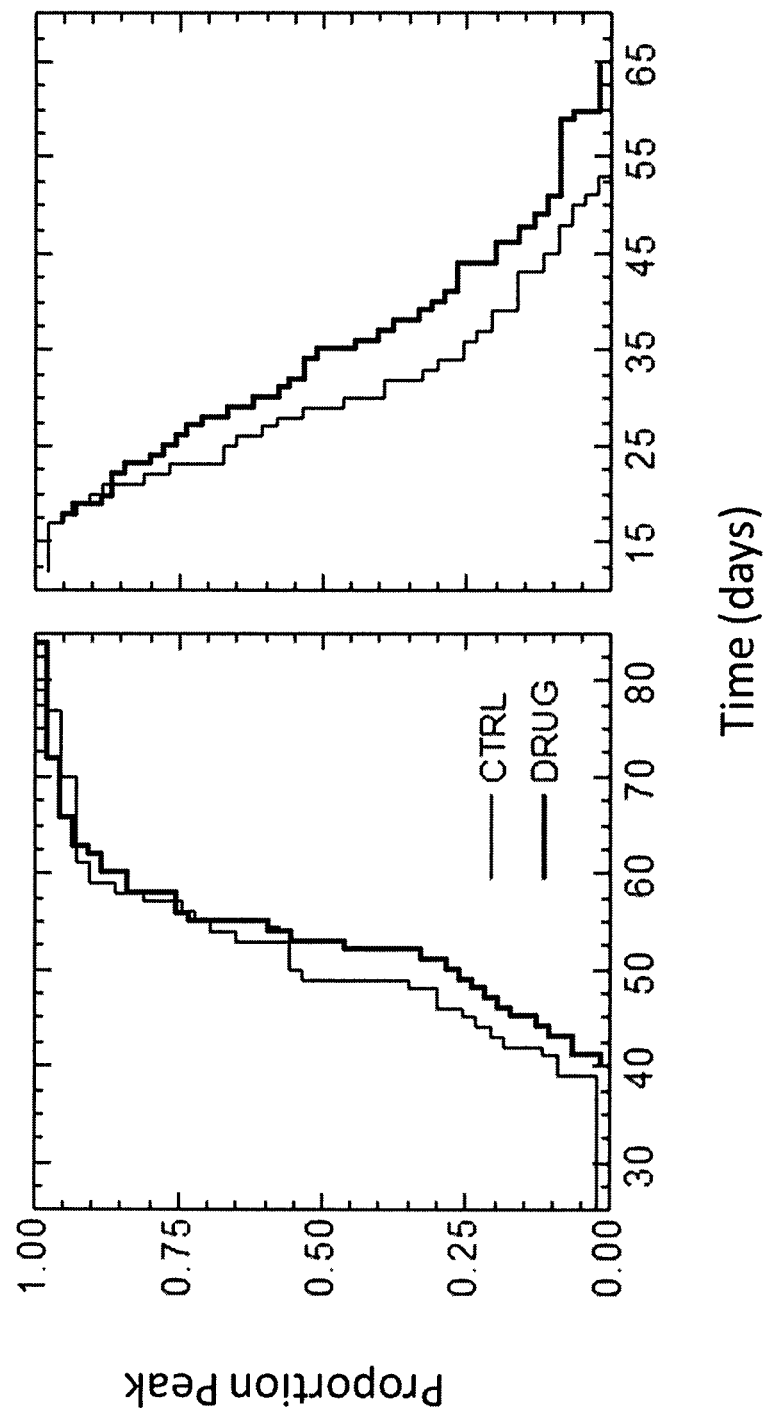
FIG. 9A is a graph of the mean daily body weight measurements starting at day 40 to attainment of peak body weight for the control group and the MR1 treated group.
FIG. 9B is a graph depicting the mean daily body weight measurements from peak body weight to death for the control group and the MR1 treated group.

Comparative MR1-treated and control group time-to-event curves for the time from day 40 to the attainment of peak body weight are shown in FIG. 9A The median time to peak body weight for the control group was 49 days compared to the MR1 treated group which was 53 days. This difference was not significant when analyzed by Kaplan Meier using the log rank and Wilcoxon statistical models, Cox proportional hazard, or parametric statistical tests.

Comparative MR1-treated and control group time-to-event curves for the time from peak body weight to death are shown in FIG. 9B. Time from peak body weight to death was statistically significantly later by 6 days in MRI treated animals. The median time from peak body weight to death in the control group was 29 days whereas in the MR1 treated group it was 35 days. Significance for each of the analyses in this example was calculated in several ways in order to better evaluate significance. The delay is statistically significant when analyzed using several statistical models: Kaplan Meier, log rank (p=0.0413) and Wilcoxon, (p=0.0732); and the Cox proportional Hazard model (p=0.0460). Based on the body weight data, MR1 appears to have less of an impact on the onset of disease in the G93A mouse model but has a dramatic effect in slowing down the rate of body weight loss from peak body weight until death.

The time-to-event plots for the age at which MR1 and control group animals progressed to a neurological score of 2 and the number of days at a neurological score of 2 is shown in FIG. 9C. The time to attain a score of 2 in the control group was 113 days and for the MR1 treated group is 121 days. Based on the neurological score data, MR1 delays disease onset in the G93A mouse model by approximately 8 days and the delay is statistically significant when analyzed using several statistical models: Kaplan Meier, log rank (p=0.0038) and Wilcoxon; (p=0.0017); and the Cox proportional hazard model, (p=0.0010).

Treated animals survival time was later by 9 days than control animals. The median survival time for the control group was 124 days and the median survival for the MR1 treated group was 133 days, as shown in FIG. 9D. The delay is statistically significant when analyzed using several statistical models: Kaplan Meier, log rank (p=0.0043) and Wilcoxon test (p=0.0040); and the Cox proportional hazard model (p=0.0030).

It is understood that the examples and embodiments described herein are for illustrative purposes only and that various modifications or changes in light thereof will be suggested to persons skilled in the art and are to be included within the spirit and purview of this application and scope of the appended claims.

The invention claimed is:

1. A method of treating a patient with Amyotrophic Lateral Sclerosis, comprising administering to the patient a therapeutically effective amount of a compound that blocks the interaction of CD40 and CD40L in combination with a compound that blocks the interaction between CD28 and CD86 or between CD28 and CD80, wherein the compound that blocks the interaction of CD40 and CD40L is an anti-CD40L antibody.

2. The method of claim 1, wherein the compound that blocks the interaction between CD28 and CD86 or between CD28 and CD80 is a CTLA4-Ig fusion protein.

3. The method of claim 1, wherein the compound that blocks the interaction between CD28 and CD86 or between CD28 and CD80 is abatacept or belatacept or galiximab.

4. The method of claim 3, wherein the compound that blocks the interaction between CD28 and CD86 or between CD28 and CD80 is abatacept or belatacept.

* * * * *